(12) United States Patent
Rajappan

(10) Patent No.: US 10,526,364 B2
(45) Date of Patent: Jan. 7, 2020

(54) IMMUNE MODULATORY COMPOSITIONS

(71) Applicant: Kumar Rajappan, San Diego, CA (US)

(72) Inventor: Kumar Rajappan, San Diego, CA (US)

( * ) Notice: Subject to any disclaimer, the term of this patent is extended or adjusted under 35 U.S.C. 154(b) by 0 days.

(21) Appl. No.: 16/103,468

(22) Filed: Aug. 14, 2018

(65) Prior Publication Data

US 2019/0055277 A1 Feb. 21, 2019

Related U.S. Application Data

(60) Provisional application No. 62/545,865, filed on Aug. 15, 2017.

(51) Int. Cl.
*C07H 21/02* (2006.01)
*A61P 35/04* (2006.01)

(52) U.S. Cl.
CPC .............. *C07H 21/02* (2013.01); *A61P 35/04* (2018.01)

(58) Field of Classification Search
CPC .................................. C07H 21/02; A61P 35/04
See application file for complete search history.

(56) References Cited

U.S. PATENT DOCUMENTS 9,549,944 B2 * 1/2017 Dubensky, Jr. ........ C07H 21/02

\* cited by examiner

*Primary Examiner* — Shirley V Gembeh
(74) *Attorney, Agent, or Firm* — Select Patents; Ashkon Cyrus

(57) ABSTRACT

A class of phosphorus containing polycyclic compounds of general formula I, of general formula I' or of general formula I", wherein $B^1$, $B^2$, $R^1$, $R^2$, $R^{1'}$, $X^1$, $X^2$, $Y^1$, $Y^2$, $B_{L1}$, $B_{L2}$, $Z^1$, and $Z^2$ are defined herein, that may be useful as modulators of type I interferon production, specifically as STING modulating agents, are provided. Also, provided are use of such compounds.

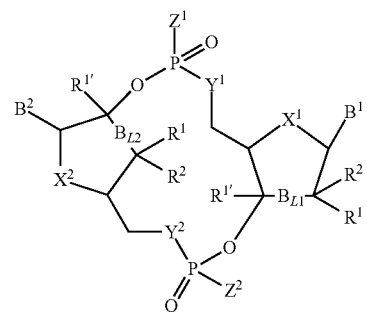

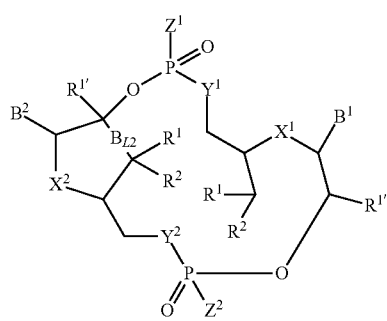

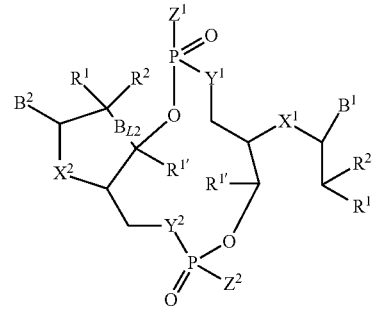

7 Claims, No Drawings

IMMUNE MODULATORY COMPOSITIONS

PRIORITY INFORMATION

This application claims priority to U.S. Provisional Application No. 62/545,865 filed Aug. 15, 2017. The content of the above application is incorporated by reference in its entirety.

FIELD OF THE INVENTION

This invention relates to cyclic dinucleotides (CDNs) and cyclic dinucleotide analogues as anticancer therapeutics, cancer vaccine adjuvants and as anti-infectious agents. Specifically, the invention concerns novel chemical compositions useful as therapeutics, vaccine adjuvants and/or immune modulators for prophylactic and/or therapeutic use in the treatment of autoimmune diseases, infectious diseases, inflammatory diseases including cancers and allergies in human or animal populations, and useful as active ingredients in pharmaceutical compositions.

BACKGROUND OF THE INVENTION

Viral and bacterial infections are major causes of morbidity and mortality in humans, accounting for a third of the deaths that occur globally each year. Certain infectious agents also cause cancer and are thought to be associated with other chronic diseases such as encephalitis and meningitis. The direct healthcare cost and indirect productivity cost associated with these diseases are very high, and affect the population disproportionately. Often, viral and bacterial infections can reach epidemic proportions in poor countries and can result in large number of deaths. Both prophylactic and therapeutic interventions are important in preventing or controlling the onslaught of infectious agents. In this respect, agents that might act as immune boosters, preferably through aiding both humoral and innate immunity, are of high importance as immune adjuvants and prophylactics.

Research suggests that cancer is an inflammatory disease often driven by the lack of sufficient immune response to check the growth and propagations of malignant cells. Thus, the lack of an adequate immune response can play a central role in all aspects of cancer growth and metastases. The relevance of the role of the immune system has been clinically validated by the clinical success and the recent approval of checkpoint inhibitors and other immuno-oncology drugs. Novel immune modulators may be effective in treating various types of cancer, and may overcome deficiencies the current checkpoint inhibitors have. Recently, cyclic dinucleotides have emerged as powerful immune modulators through their binding and activation of an endoplasmic reticulum bound protein called STING, an acronym for STimulator of INterferon Genes.

Cyclic guanosine adenosine monophosphate synthase (cGAS) is the principal pattern recognition receptor that senses pathogenic versus self DNA in the cytosol and catalyzes the production of cyclic Guanosine Adenosine MonoPhosphate (cGAMP), one of the endogenous cyclic dinucleotides (Sun, L. et al. *Science* 2013, 339, 786-791) that serves as a second messenger to activate innate immune responses (Jiaxi Wu et al. *Science* 2013, 339, 826-830). The mechanism by which cGAMP activates the immune response is through its binding to the endoplasmic reticulum bound protein STING (G. N. Barber, *Immunol. Rev.* 2011, 243, 99) and its activation. STING activation triggers a downstream signaling cascade that results in activation of cytosolic kinases IKK (I-kappa-B Kinase) and TBK1 (TANK Binding Kinase 1), which activates the transcription factors NF-kB (Nuclear Factor kappa light chain enhancer of activated B cells) and IRF3 (Interferon Regulatory Factor 3), respectively. Translocation of NF-kB and IRF3 to the nucleus leads to the induction of type I interferons. Type I interferon induction has functional consequences for the treatment of cancer, viral diseases and bacterial infections. Following examples of STING modulators, specifically STING agonists, described in the art mainly concern 1) cancer immunotherapy and 2) anti-viral therapy. However, STING modulators may be useful in treating many types of autoimmune diseases, inflammatory conditions and bacterial infections, as will be described in the present disclosure.

Cancer Immunotherapy: Many recent high impact publications have underscored the effectiveness of STING activation as a non-specific cancer immunotherapy paradigm, and its translational capability has been highlighted. For example, Fu et al. found that co-administration of cyclic dinucleotides with a cellular cancer vaccine called STINGVAX was effective against multiple types of tumors in mouse models. Furthermore, they showed that stronger STING binding through chemical modification of CDNs increased antitumor activity (*Science Translational Medicine,* 2015, 7, pp. 283ra52). Another report by Corrales et al. demonstrated that intra-tumoral injection of CDNs activated STING-interferon-cytotoxic T-cell pathway and induced profound regression of established tumors in mice, and generated substantial systemic immune responses capable of rejecting distant metastases and providing long-lived immunologic memory (*Cell Reports,* 2015, 11, 1-13). According to these authors, "synthetic CDNs have high translational potential as a cancer therapeutic." The emerging field of CDN based cancer immunotherapy has great potential not only as cancer vaccine adjuvants, but also as powerful cancer drugs in combination with checkpoint inhibitors. However, checkpoint inhibitors are not universally effective; they are not very effective in tumors where the immune system fail to recognize cancer cells as dangerous. But, combining checkpoint inhibitors and STING agonists have proven to be effective in killing even distant metastases (*Science Translational Medicine,* 2015, 7, pp. 283ra52). The present disclosure addresses these previous problems in the art and is in part directed towards CDNs acting as powerful anticancer immune stimulants, either alone or in combinations with other immuno-oncology therapeutics and/or chemotherapeutics, and/or DNA hypomethylating agents.

Anti-Viral Therapy using STING Agonists—Treating HBV infection as an example: Chronic hepatitis B virus (HBV) infection is notoriously difficult to treat, let alone cure, in spite of a number of nucleoside analogues (Nucs) available in the market. Long term treatment with Nucs and interferon is known to have therapeutic effect. However, HBV surface antigen (HBsAg) seroconversion, the sign of a successful immunologic control of HBV, or a "functional cure," is rarely achieved with the current therapies. With over 400 million people chronically infected with HBV worldwide, the number of cases of liver fibrosis, cirrhosis and hepatocellular carcinoma resulting from long term infection is rising at an alarming rate. Thus, there is a need for effective anti HBV therapy that is robust and sustainable enough to clear the host incorporated viral genome. Recent reports suggest (Guo F, et al. *Antimicrob Agents Chemother.* 2015, 59, 1273-81) that the restoration of host innate and HBV-specific adaptive immune responses may be essential for a functional cure of chronic HBV infection (Chang J, et al. *Antiviral Res* 96:405-413).

Chronic HBV infection results from failed immune response to the onset of HBV infection. Typically, pathogen associated molecular patterns (PAMP) are sensed by host mediated pattern recognition receptors (PRRS) and puts up a strong immune response. But HBV has been shown to induce negligible innate immune responses during the early phase of infection. In fact, Type I interferon (IFN), a hallmark of antiviral innate signaling, is either undetectable or missing in most cases of HBV patients, and there is no concrete evidence that IFNs are produced in HBV patients (Dunn C, et al. *Gastroenterology* 2009, 137, 1289-1300). Yet, evidence suggests that HBV is sensitive to ligand mediated activation of STING-IFN pathway, and resulting antiviral response is strong and sustainable (Guo F, et al. *Antimicrob Agents Chemother.* 2015, 59, 1273-81). Another report has revealed that STING is a new target of the viral polymerase to antagonize the IFN induction against HBV (Liu Y, et al. *J. Virol.* 2015, 89, 2287-2300). When this is coupled with the fact that STING agonists induce an innate antiviral immune response against HBV, it may be possible that a viral polymerase inhibitor such as ribavirin or entecavir or any other Nucs and a CDN might have the double effect of stopping replication and providing immune boost through STING activation. From a clinical perspective, it is possible to 'sandwich' a STING agonist treatment with Nuc therapy that clears most of the virus, followed by STING therapy effectively clearing HBV cccDNA (covalently closed circular DNA) (interferon is produced in the nucleus), which will again be followed by nuc therapy to clear any mature virus that may have entered the cytosol. In another aspect, a CDN STING agonist can be specifically and selectively delivered to liver cells, thus restricting the systemic effect of the drug. This approach can achieve two objectives: 1) decreased toxicity to other healthy organs due to decreased dose and 2) improved efficacy due to selective delivery to hepatocytes, the host cells of HBV.

The present disclosure is intended to provide novel STING agonists/modulators as prophylactics and/or therapeutics in the treatment of cancers, viral diseases and bacterial infections.

SUMMARY OF THE INVENTION

Embodiments of the present invention include STING agonists and STING antagonists or STING binding ligands or STING modulators in general, and are further illustrated by the classes, subclasses, and species disclosed herein.

The compounds disclosed herein have several advantages over naturally occurring cyclic dinucleotides (CDNs) or other modified CDNs because they may be able to activate one or more known human STING alleles. Further embodiments are provided for treating diseases in a subject, comprising administering to the subject an effective amount of a compound as described herein. Such compounds may be used as STING agonists or antagonists. In further embodiments, there are provided compositions and methods concerning methods for treating cancer in a subject comprising administering to the subject an effective amount of a stimulator of interferon genes (STING) agonist, wherein the STING agonist is administered intratumorally.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention and are defined by the scope of the claims.

The abbreviations used herein have their conventional meaning as known to the practitioner of chemistry and biology and within the chemical and biological arts. The chemical structures and formulae set forth herein are constructed according to the conventional rules of chemical valency known in the chemical arts.

The chemical structures disclosed herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all possible tautomers of the compounds of the invention are within the scope of the invention. Additionally, unless otherwise stated, structures depicted herein include compounds that one may obtain by enriching one or more atoms. For example, any compounds with the replacement of one or more hydrogen atoms by deuterium or tritium, or the replacement of a carbon atom by a $^{13}$C- or $^{14}$C-enriched carbon are within the scope of this invention. Such compounds may be used as, for example, analytical tools, probes in biological assays, or therapeutic agents in accordance with the present invention.

The following definitions shall apply unless otherwise indicated. For purposes of this disclosure, the chemical elements are identified in accordance with the Periodic Table of the Elements, IUPAC version, dated 1 May 2013. Additionally, general principles of organic chemistry are described in "Organic Chemistry", T. W. Graham Solomons, Craig B. Fryhle, Scott A. Snyder, Wiley; 11$^{th}$ edition (Jan. 17, 2013) and "March's Advanced Organic Chemistry", 5th Ed., Ed.: Smith, M. B. and March, J., John Wiley & Sons, New York: 2001, the entire contents of which are hereby incorporated by reference.

The terms "Treatment" or "treating" includes (1) Curing a disease in a subject or patient experiencing or displaying the pathology or symptomatology of the disease (e.g. eliminating the diseases) (2) inhibiting further progression in a subject or patient of the pathology and/or symptomatology, (3) ameliorating a disease in a subject or patient that is experiencing or displaying the pathology or symptomatology of the disease (e.g., reversing the pathology and/or symptomatology), (4) effecting any measurable decrease in a disease in a subject or patient that is experiencing or displaying the pathology or symptomatology of the disease and/or (5) eliminating or suppressing the presence of a pathogen that is causative of a disease (e.g. eliminating hepatitis B virus in a subject infected with hepatitis B virus and showing pathology and symptoms of hepatitis B virus infection). In some embodiments, treating cancer is further defined as reducing the size of a tumor or inhibiting growth of a tumor or eliminating the presence of a tumor. In particular embodiments, the subject is a human.

In some embodiments the treatment may comprise of administering the compositions or compounds described herein to a subject in need thereof by a variety of routes in formulations containing pharmaceutically acceptable carriers, adjuvants and vehicles. Such administration routes may be systemic or local and may include, but not limited to, parenteral, intratumoral, subcutaneous, intravenous, intramuscular, intraarterial, intradermal, intrathecal, intranasal, intraperitoneal, intra-cerebroventricular, and epidural administrations.

In another embodiment, use of STING agonists along with chemotherapy are provided. For example, anthracyclins can improve efficacy of immunotherapy by increasing the sensitivity of tumor cells to CD8 positive T cells, also called immune effector cells or cytotoxic T cells (Zhang et al. *Cancer Letters* 2015, 369, 331-335). Anthracyclines are also known to eliminate myeloid derived suppressor cells (MDSCs) which are known immune suppressants (Alizadeh et al. *Cancer Research* 2014, 74, 104-118). Further embodiments include the use of following chemotherapy drugs with STING modulators of the present invention: Doxorubicin, Doxil, epirubicin, daunorubicin, cyclophosphamide, ara-C, ara-A, 5-FU, capecitabin, oxaliplatin, carboplatin, paclitaxel, campothesin, irinotecan, topotecan, Abraxane, vincristine, vinblastine and celecoxib.

Another embodiment includes the use of epigenetic modulators, such as DNA methyl transferase (DNMT) inhibitors and histone deacetylase (HDAC) inhibitors, in combination with STING modulators for cancer immunotherapy. De novo methylation of immune related genes is known to support T cell exhaustion which is a primary reason for immune suppression against cancer cells. Inhibition of de novo methylation in immune cells has shown CD8 positive T cell rejuvenation and improved cancer cell killing (Ghoneim et al. *Cell* 2017, 170, 142-157). Thus, embodiments include the following drugs used in combination therapy with STING agonists: Vidaza (5-azacytidine), decitabine, guadecitabine, zebularine, 2'-deoxyzebularine, varinostat, trichostatin A, panobinostat, sodium butyrate and romidepsin.

Unless otherwise specified, both D- and L-stereoisomers of the declared structures, and mixtures thereof, are within the scope of this disclosure. The term "acyl," as used herein, represents a hydrogen or an alkyl group that is attached to the parent molecular group through a carbonyl group, as defined herein, and is exemplified by formyl, acetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

The term "aliphatic" or "aliphatic group", as used herein, means a straight-unbranched carbon chain or branched carbon chain, substituted or unsubstituted carbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclic," "cycloaliphatic" or "cycloalkyl"), that has a single point of attachment to the rest of the molecule. Unless otherwise specified, aliphatic groups may contain 1-12 aliphatic carbons atoms, 1-10 aliphatic carbon atoms, 1-8 aliphatic carbon atoms or 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched.

The term "heteroatom" means one or more of oxygen, sulfur, nitrogen, phosphorus, boron, or silicon (including, any oxidized form of nitrogen, sulfur, phosphorus, or silicon; a quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in some embodiments alkyl groups contain 1-3 carbon atoms, and in some embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tertiary-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of set of hydrogen atoms. Unless otherwise specified, alkenyl groups contain 2-12 carbon atoms. In certain embodiments, alkenyl groups contain 2-8 carbon atoms. In certain embodiments, alkenyl groups may contain 2-6 carbon atoms, 2-5 carbon atoms, 2-4 carbon atoms, 2-3 carbon atoms, and in some embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in some embodiments alkynyl groups contain 2-3 carbon atoms, and in some embodiments alkynyl groups contain 2 carbon atoms. Representative alkynyl groups include, but are not limited to, ethynyl, 2-propynyl (propargyl), 1-propynyl, and the like.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below.

The term "halo," as used herein, represents a halogen selected from bromine, chlorine, iodine, or fluorine. The term "halogen" means F, Cl, Br, or I.

The term "haloalkoxy," as used herein, represents an alkoxy group, as defined herein, substituted by a halogen group (i.e., F, Cl, Br, or I). A haloalkoxy may be substituted with one, two, three halogens. In the case of alkyl groups of two carbons or more, haloalkoxy may be substituted with one, two, three, four, five or six halogens.

Haloalkoxy groups include perfluoroalkoxys (e.g., —OCF$_3$, —OCHF$_2$, —OCH$_2$F, —OCCl$_3$, —OCH$_2$CH$_2$Br, —OCH$_2$CH(CH$_2$CH$_2$Br)CH$_3$, —OCHICH$_3$, and —OCF$_2$CF$_3$). In some embodiments, the haloalkoxy group can be further substituted with 1, 2, 3, or 4 substituent groups as described herein for alkyl groups. The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —CF$_3$), —CHF$_2$, —CH$_2$F, —CH$_2$CH$_2$Br, —CH$_2$CH(CH$_2$CH$_2$Br)CH$_3$, —CHICH$_3$ and —CF$_2$CF$_2$. In some embodiments, the haloalkyl group can be further substituted with 1, 2, 3, or 4 substituent groups as described herein for alkyl groups.

The term "aryl" used alone or as part of a larger moiety as in "aralkyl," "aralkoxy," or "aryloxyalkyl," refers to monocyclic and bicyclic ring systems having a total of five to ten ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 n electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one.

A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multi-cyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6- dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo, 4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3, 7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed here.

The term "protecting group," as used herein, refers to a chemically labile chemical moiety that is known in the art to temporarily block chemically reactive functional groups including, but not limited to, hydroxyl, amino and thiol groups, against undesired reactions during synthetic procedures. Protecting groups are typically used selectively and/or orthogonally to prevent reactivity of selected reactive sites during reactions at desired alternate reactive sites and can then be removed to leave the unprotected group as is or available for further reactions. Generally, groups are protected that will be inert to reactions that modify other areas of the parent molecule for conversion into their original groups at an appropriate time. Protecting groups as known in the art are described generally in Peter G. M. Wuts and Theodora W. Greene, Greene's Protective Groups in Organic Synthesis, 4$^{th}$ edition, John Wiley & Sons, New York (2007).

Examples of hydroxyl protecting groups include, but are not limited to, acetyl, benzoyl, t-butyl, t-butoxymethyl, 4-dinitrophenyl, benzyl, 2,6-dichlorobenzyl, diphenylmethyl, p-nitrobenzyl, bis(2-acetoxyethoxy)methyl (ACE), 2-trimethyl silylethyl, diphenylsilyl, triphenylsilyl, [(triisopropylsilyl)oxy]methyl (TOM), benzoylformate, chloroacetyl, trichloroacetyl, trifluoroacetyl, pivaloyl, p-phenylbenzoyl, 9-fluorenyl methyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX), benzyl, 2,6-dichlorobenzyl, t-butyldimethylsilyl, t-butyldiphenylsilyl, benzoyl, mesylate, tosylate, 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, phenoxyacetyl (Pac), trihaloacetyl, benzoyl, isobutyryl, and nitrophenylacetyl; sulfonamide-protecting groups, such as 2-nitrobenzenesulfonyl; imine- and cyclic imide-protecting groups, such as phthalimido and dithiasuccinoyl; primary amine protecting groups such as N-(1-(4,4-dimethyl-2,6-dioxocyclohexylidene)ethyl) (Dde) and trifluoroacetyl.

The term "ligand" means a chemical moiety that acts as a substrate or a binding partner for a naturally occurring receptor on the cell surface, an enzyme in the blood stream or in the cytosol or any other cellular compartments such as nucleus, mitochondria, Golgi apparatus, ribosome etc., or a naturally occurring transporter protein that typically transports amino acids, peptides, hormones, carbohydrates, vitamins, ions like sodium, potassium etc. and nucleosides and nucleoside analogs etc. across the cell membrane. Such ligand binding can lead to changes on such receptors, enzymes and transporters temporarily such that ligands might get internalized into the cell, might undergo structural transformation, or might get transported across the cell membrane.

The term "conjugate" means a larger chemical moiety formed by covalent bonding of two or more smaller chemical moieties with distinct structures and functions through a linker moiety. In the case of a ligand-CDN conjugate, a cyclic dinucleotide and a ligand, e.g. a folic acid moiety, are covalently linked together through a linker moiety.

The term "linker" means a chemical moiety that connects a "ligand" and a CDN. Such linkers can be a straight carbon chain of a series of methylene groups, a molecule incorporating an ester, amide, carbamate, carbonate, triazole, disulfide, thioester, ether, ethylene glycol, polyethylene glycol, secondary amine, tertiary amine, aromatic or hetero-aromatic groups or a combination of these of these groups. Such linkers preferably have stability in the blood stream so that the ligand-CDN conjugate is intact while in circulation, but gets hydrolyzed once inside the cell or diseased tissue.

The term "CDN" means a cyclic dinucleotide.

The term "derivative" means chemical and structural form of a naturally occurring or synthetic ligand that has been chemically modified to be attached to a drug through a covalent bond.

The terms "modulators" may mean either an agonist or an antagonist or a binding ligand. As an agonist the modulator increases the expression or functions of a biological factor. As an antagonist the modulator works against or works to decrease the expression or function of a biological factor. A binding ligand simply binds to the biological factor through chemical interactions such as hydrophobic, hydrophilic, hydrogen bonding, van der waals bonding. Therefore, the terms "modulators" are interchangeable with "agonists" or "antagonists" or "binding ligand" depending on the binding affinity and mode of binding to the biological factor. The biological factor in the present application is the adaptor protein STING.

Other objects, features and advantages of the present invention will become apparent from the following detailed description. It should be understood, however, that the detailed description and the specific examples, while indicating preferred embodiments of the invention, are given by way of illustration only, as various changes and modifications within the spirit and scope of the invention will become apparent to those skilled in the art from this detailed description.

DETAILED DESCRIPTION

Embodiments of the present invention include STING agonists and STING antagonists or STING binding ligands or STING modulators in general as described generally above, and are further illustrated by the classes, subclasses, and species disclosed herein. Other objects, features and advantages of the present invention will become apparent from the following detailed description. It should be understood, however, that the detailed description and the specific examples, while indicating preferred embodiments of the invention, are given by way of illustration only, as various changes and modifications within the spirit and scope of the invention will become apparent to those skilled in the art from this detailed description.

In the present patent application, a series of cyclic dinucleotide (CDN) analogs having general formulae I, I' and I" which are further defined below in detail, and their corresponding pharmaceutically acceptable salts, compositions, prodrugs and dosage forms and ligand-CDN conjugates thereof are claimed.

In some embodiments, the present invention provides compounds of formula I, and their corresponding pharmaceutically acceptable salts, compositions, prodrugs, dosage forms and conjugates thereof.

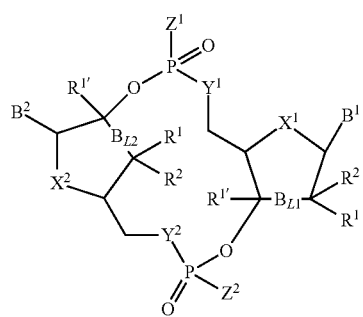

I wherein:

$B^1$ and $B^2$ are independently and optionally selected from the group consisting of:

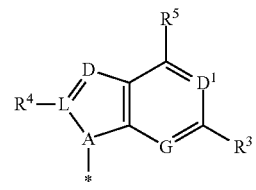

II

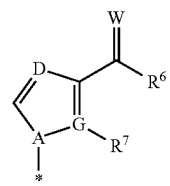

III

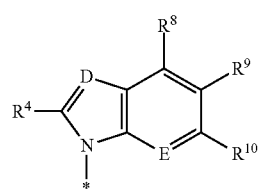

IV

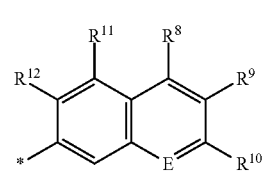

V

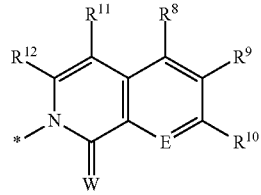

VI

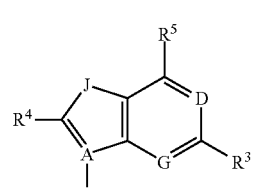

VII

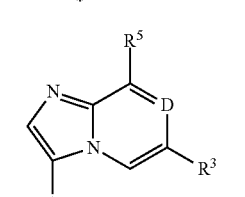

VIII

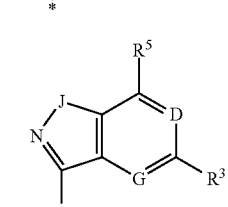

IX

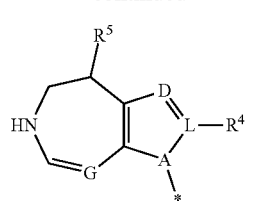
X

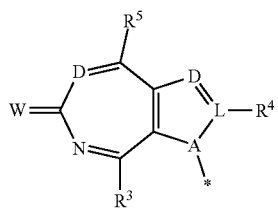
XI

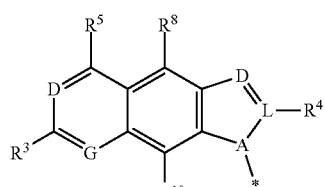
XII

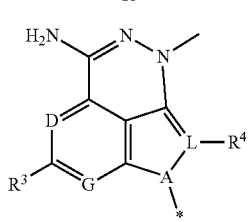
XIII

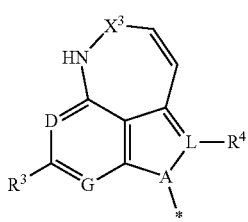
XIV

Wherein, each $R^3$, $R^4$, $R^5$, $R^8$, $R^9$, $R^{10}$, $R^1$ and $R^{12}$ is independently and optionally selected from a group consisting of hydrogen, halogen, —$NO_2$, —CN, R, —OR, —SR, —NHR, —$N(R)_2$, —C(O)R, —$CO_2R$, —C(O)C(O)R, —C(O)$CH_2$C(O)R, —S(O)R, —S(O)$_2$R, —C(O)N(R)$_2$, —$SO_2N(R)_2$, —OC(O)R, —N(R)C(O)R, —N(R)C(=NR)N(R)$_2$, —C(=NR)N(R)$_2$, —C=NOR, —N(R)SO$_2$N(R)$_2$, —N(R)SO$_2$R, —OC(O)N(R)$_2$, or an optionally substituted group selected from $C_{1-12}$ aliphatic, phenyl, a 3-6 membered saturated or partially unsaturated monocyclic carbocyclic ring, a 3-6 membered saturated or partially unsaturated heterocyclic ring having 1-2 heteroatoms independently selected from nitrogen, oxygen, or sulfur, and a 5-6 membered heteroaryl ring having 1-3 heteroatoms independently selected from nitrogen, oxygen, or sulfur.

$R^6$ is independently $NH_2$, NHR, OH, —OR, —SR, —N(R)$_2$.

$R^7$ is independently halogen, $NH_2$, NHR, OH, OR, SH, SR, —N(R)$_2$ when G is a C, and $R^7$ is absent when G is N.

Each R is independently selected from the group consisting of hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, and a 5-6 membered heteroaryl ring having 1-3 heteroatoms independently selected from nitrogen, oxygen, or sulfur; or: two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur.

A, E and G are independently N, C, $CR^a$ where $R^a$ is independently a halogen or H.

D is independently selected from N, CH, C—CN, C—$NO_2$, CR, C—$NH_2$, C—NHR, CN(R)$_2$, CF, Cl, C—CONH$_2$, C—CONHR, C—CON(R)$_2$, C—CSN(R)$_2$, C—COOR, C—C(=NH)NH$_2$, C—OH, C—OR, C—$C_{1-4}$ alkylamino, C-di($C_{1-4}$ alkyl)amino, C-(1,3-oxazol-2-yl), C-(1,3-thiazol-2-yl), or C-(imidazol-2-yl); Wherein alkyl is optionally substituted with one to three groups independently selected from halogen, amino, hydroxyl, carboxyl, or $C_{1-3}$ alkoxy.

$D^1$ is independently selected from N, CH, C—CN, C—$NO_2$, CR, C—$NH_2$, C—NHR, CN(R)$_2$, CF, Cl, C—CONH$_2$, C—CONHR, C—CON(R)$_2$, C—CSN(R)$_2$, C—COOR, C—C(=NH)NH$_2$, C—OH, C—OR, C—$C_{1-4}$ alkylamino, C-di($C_{1-4}$ alkyl)amino, C-(1,3-oxazol-2-yl), C-(1,3-thiazol-2-yl), or C-(imidazol-2-yl); Wherein alkyl is optionally substituted with one to three groups independently selected from halogen, amino, hydroxyl, carboxyl, or $C_{1-3}$ alkoxy.

J is independently selected from O, S, $SO_2$, NH or NR.

L is independently selected from C or N; wherein when L is N, $R^4$ is absent and when L is C, $R^4$ is as defined above.

W is independently O, S or NH.

$R^1$ and $R^2$ are independently and optionally selected from the group consisting of hydrogen, halogen, —$NO_2$, —CN, —OR, —SR, —NHR, —N(R)$_2$, —C(O)R, —$CO_2R$, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, and optionally substituted $C_{1-12}$ aliphatic or $C_{1-4}$ alkoxy-$C_{1-4}$ alkyl;

$R^1$ and $R^2$ cannot be the same except for hydrogen.

$B_{L1}$ and $B_{L2}$ are independently and optionally a bond connecting the two carbons attached to each of them.

Either $B_{L1}$ or $B_{L2}$ may be optionally absent or both $B_{L1}$ and $B_{L2}$ may be absent such that no C—C bond exists Both $B_{L1}$ and $B_{L2}$ cannot be a bond at the same time in the same molecule Each $R^{1'}$ are independently and optionally selected from a group consisting of hydrogen, halogen, $N_3$, C(O)OH, CN, C(O)NH$_2$, C(S)NH$_2$, C(O)OR or R.

$X^1$ and $X^2$ are independently and optionally for each occurrence an O, S, NH, NR, CH$_2$, CHR, C(R)$_2$, C=CH$_2$, or C=CF$_2$ $X^3$ may independently and optionally be selected from, O, NH, C=O, SO$_2$, C=NH, NR $Y^1$ and $Y^2$ is independently and optionally for each occurrence an O, S, NH, CH$_2$, CF$_2$ or CCl$_2$ $Z^1$ and $Z^2$ are independently selected from: O$^-$, S$^-$, OH, SH, H, CH$_3$, F, BH$_3^-$.

Alternatively, $Z^1$ and $Z^2$ are independently selected from OL$^2$, OCH$_2$CH$_2$L$^2$, OCH$_2$OC(O)L$^2$, OCH$_2$OC(O)NHL$^2$, OCH$_2$OC(O)N(L$^2$)$_2$, OCH$_2$OC(O)OL$^2$, OCH$_2$OC(O)SL$^2$, OCH$_2$NHC(O)L$^2$, OCH$_2$SC(O)L$^2$, OCH$_2$(CH$_2$)$_{1-6}$OC(O)L$^2$, OCH$_2$(CH$_2$)$_{1-6}$SC(O)L$^2$, OCH$_2$(CH$_2$)$_{1-6}$NHC(O)L$^2$, $OCH_2(CH_2)_{1-6}OC(O)OL^2$, $OCH_2(CH_2)_{1-6}SC(O)OL^2$, $OCH_2(CH_2)_{1-6}NHC(O)OL^2$, $OCH_2O(CO)C(CH_3)_3$, $OCH_2O(CO)C(CH_3)_2CH_2OL^2$, $OCH_2S(CO)C(CH_3)_2CH_2OL^2$, $OCH_2CH_2O(CO)C(CH_3)_3$, $OCH_2CH_2S(CO)C(CH_3)_3$, $OCH_2CH_2O(CO)C(CH_3)_2CH_2OL^2$, $OCH_2CH_2S(CO)C(CH_3)_2CH_2OL^2$, $OCH_2CH_2S—SCH_2(CH_2)_{0-6}L^2$, $OCH_2CH_2S—SCH_2(CH_2)_{0-6}OL^2$, $—O(CH_2CH_2O)_{2-20}L^2$, $—O(CH_2CH_2O)_{2-20}C(O)OL^2$, $O(CH_2CH_2O)_{2-20}C(O)NHL^2$, $—O(CH_2CH_2O)_{2-20}CH_2CH_2NHC(O)L^2$, $—O(CH_2CH_2O)_{2-20}C(O)N(L^2)_2$, $—S(CH_2CH_2O)_{2-20}L^2$, $—S(CH_2CH_2O)_{2-20}C(O)OL^2$, $—S(CH_2CH_2O)_{2-20}C(O)NHL^2$, $—S(CH_2CH_2O)_{2-20}C(O)N(L^2)_2$.

Where $L^2$ is independently and optionally selected from any of the following: H, $N_3$, $C_{1-20}$ straight chain alkyl, a $C_{1-20}$ straight chain alkenyl, $C_{1-20}$ alkynyl, $C_{3-6}$ cycloalkyl, $C_{1-6}$ haloalkyl, a tert-butyl, a substituted tert-butyl, a glucuronide moiety, (J. Med. Chem. 1999, 42, 3623-3628), a tyrosine, a tyrosine derivative, a lipid, a dehydroascorbic acid derivative, a N-acetylgalactosamine derivative, a glucose derivative, a galactose derivative, a mannose derivative, a fatty acid derivative, a natural peptide comprising of 2-13 amino acids, a modified peptide comprising of 2-13 amino acids, a sigma-2 receptor binding ligand derivative, a retinoic acid derivative, a prostate specific membrane antigen (PSMA) binding ligand derivative, a folic acid derivative, a glycirrhetinic acid (GA) receptor binding ligand derivative, an Asialo Glycoprotein Receptor (ASGPR) binding ligand derivative or a chemical derivative that allows selective uptake by a cell through a preferentially expressed receptor or transporter that exists on the cell surface.

In some other embodiments, the present invention provides compounds of formula I', and its corresponding pharmaceutically acceptable salts, compositions, prodrugs, dosage forms and CDN-ligand conjugates thereof.

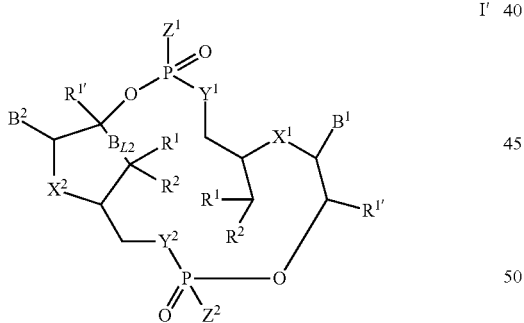

I'

Wherein:

$B^1$ and $B^2$ are independently and optionally selected from the group consisting of:

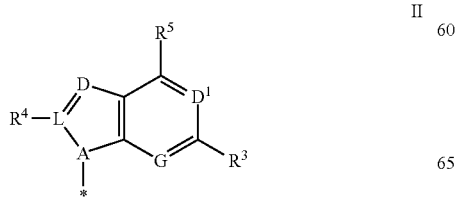

II

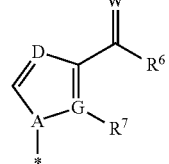

III

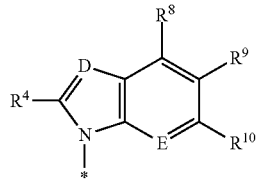

IV

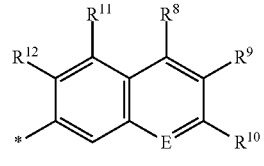

V

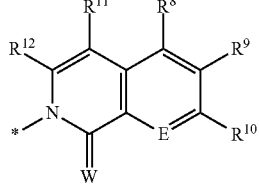

VI

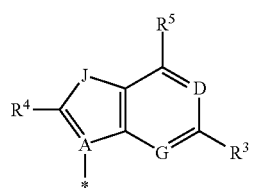

VII

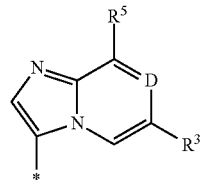

VIII

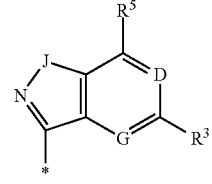

IX

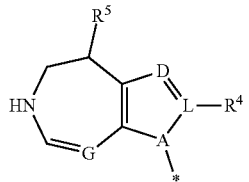

X

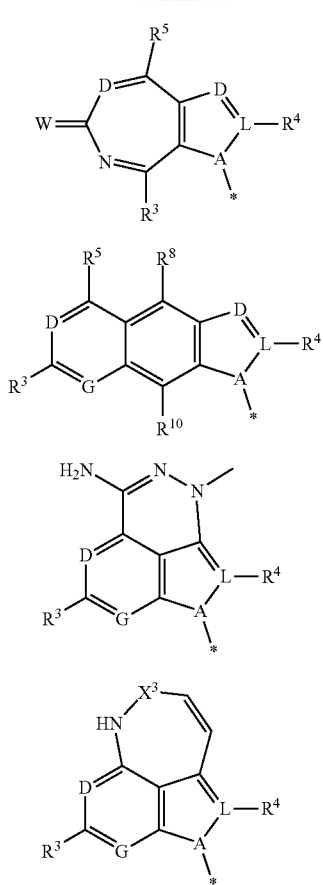

each R[1] and R[2] are independently and optionally selected from the group consisting of hydrogen, halogen, —NO$_2$, —CN, —OR, —SR, —NHR, —N(R)$_2$, —C(O)R, —CO$_2$R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, C(=NR)N(R)$_2$, —C=NOR, —N(R)C(O)N(R)$_2$, —N(R)SO$_2$N(R)$_2$, —N(R)SO$_2$R, —OC(O)N(R)$_2$, and optionally substituted C$_{1-12}$ aliphatic or C$_{1-4}$ alkoxy-C$_{1-4}$ alkyl;

R[1] and R[2] cannot be the same except for hydrogen.

B$_{L2}$ is a bond connecting the two carbons attached to it or optionally not a bond.

Each R[1'] are independently and optionally selected from a group consisting of hydrogen, halogen, N$_3$, C(O)OH, CN, C(O)NH$_2$, C(S)NH$_2$, C(O)OR or R.

Each R[3], R[4], R[5], R[8], R[9], R[10], R[11] and R[12] is independently and optionally selected from a group consisting of hydrogen, halogen, —NO$_2$, —CN, R, —OR, —SR, —NHR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)C(=NR)N(R)$_2$, —C(=NR)N(R)$_2$, —C=NOR, —N(R)SO$_2$N(R)$_2$, —N(R)SO$_2$R, —OC(O)N(R)$_2$, or an optionally substituted group selected from C$_{1-12}$ aliphatic, phenyl, a 3-6 membered saturated or partially unsaturated monocyclic carbocyclic ring, a 3-6 membered saturated or partially unsaturated heterocyclic ring having 1-2 heteroatoms independently selected from nitrogen, oxygen, or sulfur, and a 5-6 membered heteroaryl ring having 1-3 heteroatoms independently selected from nitrogen, oxygen, or sulfur.

R[6] is independently NH$_2$, NHR, OH, —OR, —SR, —N(R)$_2$

R[7] is independently halogen, NH$_2$, NHR, OH, OR, SH, SR, —N(R)$_2$ when G is a C, and R[7] is absent when G is N.

Each R is independently selected from the group consisting of hydrogen or an optionally substituted group selected from C$_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, and a 5-6 membered heteroaryl ring having 1-3 heteroatoms independently selected from nitrogen, oxygen, or sulfur; or: two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur.

A, E and G are independently N, C, CR$^a$ where R$^a$ is independently halogen or H.

D is independently selected from N, CH, C—CN, C—NO$_2$, CR, C—NH$_2$, C—NHR, CN(R)$_2$, CF, CI, C—CONH$_2$, C—CONHR, C—CON(R)$_2$, C—CSN(R)$_2$, C—COOR, C—C(=NH)NH$_2$, C—OH, C—OR, C—C$_{1-4}$ alkylamino, C-di(C$_{1-4}$ alkyl)amino, C-(1,3-oxazol-2-yl), C-(1,3-thiazol-2-yl), or C-(imidazol-2-yl); Wherein alkyl is optionally substituted with one to three groups independently selected from halogen, amino, hydroxyl, carboxyl, or C$_{1-3}$ alkoxy.

D[1] is independently selected from N, CH, C—CN, C—NO$_2$, CR, C—NH$_2$, C—NHR, CN(R)$_2$, CF, CI, C—CONH$_2$, C—CONHR, C—CON(R)$_2$, C—CSN(R)$_2$, C—COOR, C—C(=NH)NH$_2$, C—OH, C—OR, C—C$_{1-4}$ alkylamino, C-di(C$_{1-4}$ alkyl)amino, C-(1,3-oxazol-2-yl), C-(1,3-thiazol-2-yl), or C-(imidazol-2-yl); Wherein alkyl is optionally substituted with one to three groups independently selected from halogen, amino, hydroxyl, carboxyl, or C$_{1-3}$ alkoxy.

J is independently selected from O, S, SO$_2$, NH or NR.

In structure II, L is independently selected from C or N; wherein when L is N, R[4] is absent and when L is C, R[4] is as defined above.

W is independently O, S or NH.

X[1] and X[2] are independently and optionally for each occurrence an O, S, NH, NR, CH$_2$, CHR, C(R)$_2$, C=CH$_2$, or C=CF$_2$.

X[3] may independently and optionally be selected from, O, NH, C=O, SO$_2$, C=NH, NR Y[1] and Y[2] is independently and optionally for each occurrence an O, S, NH, CH$_2$, CF$_2$ or CCl$_2$ Z[1] and Z[2] are independently selected from: O$^-$, S$^-$, OH, SH, H, CH$_3$, F, BH$_3^-$. It can be appreciated that the negative charges are balanced by positive counter ions to form pharmaceutically acceptable salts.

Alternatively, Z[1] and Z[2] are independently selected from OL[2], OCH$_2$CH$_2$L[2], OCH$_2$OC(O)L[2], OCH$_2$OC(O)NHL[2], OCH$_2$OC(O)N(L[2])$_2$, OCH$_2$OC(O)OL[2], OCH$_2$OC(O)SL[2], OCH$_2$NHC(O)L[2], OCH$_2$SC(O)L[2], OCH$_2$(CH$_2$)$_{1-6}$OC(O)L[2], OCH$_2$(CH$_2$)$_{1-6}$SC(O)L[2], OCH$_2$(CH$_2$)$_{1-6}$NHC(O)L[2], OCH$_2$(CH$_2$)$_{1-6}$OC(O)OL[2], OCH$_2$(CH$_2$)$_{1-6}$SC(O)OL[2], OCH$_2$(CH$_2$)$_{1-6}$NHC(O)OL[2], OCH$_2$O(CO)C(CH$_3$)$_3$, OCH$_2$O(CO)C(CH$_3$)$_2$CH$_2$OL[2], OCH$_2$S(CO)C(CH$_3$)$_2$CH$_2$OL[2], OCH$_2$CH$_2$O(CO)C(CH$_3$)$_3$, OCH$_2$CH$_2$S(CO)C(CH$_3$)$_3$, OCH$_2$CH$_2$O(CO)C(CH$_3$)$_2$CH$_2$OL[2], OCH$_2$CH$_2$S(CO)C(CH$_3$)$_2$CH$_2$OL[2], OCH$_2$CH$_2$S—SCH$_2$(CH$_2$)$_{0-6}$L[2], OCH$_2$CH$_2$S—SCH$_2$(CH$_2$)$_{0-6}$OL[2], O(CH$_2$CH$_2$O)$_{2-20}$L[2], —O(CH$_2$CH$_2$O)$_{2-20}$C(O)OL[2], —O(CH$_2$CH$_2$O)$_{2-20}$ C(O)NHL$^2$, —O(CH$_2$CH$_2$O)$_{2-20}$ CH$_2$CH$_2$NHC(O)L$^2$, —O(CH$_2$CH$_2$O)$_{2-20}$ C(O)N(L$^2$)$_2$, —S(CH$_2$CH$_2$O)$_{2-20}$L$^2$, —S(CH$_2$CH$_2$O)$_{2-20}$C(O)OL$^2$, —S(CH$_2$CH$_2$O)$_{2-20}$ C(O)NHL$^2$, —S(CH$_2$CH$_2$O)$_{2-20}$ C(O)N(L$^2$)$_2$.

Where L$^2$ is independently and optionally selected from any of the following: H, N$_3$, C$_{1-20}$ straight chain alkyl, a C$_{1-20}$ straight chain alkenyl, C$_{1-20}$ alkynyl, C$_{3-6}$ cycloalkyl, C$_{1-6}$ haloalkyl, a tert-butyl, a substituted tert-butyl, a glucuronide moiety, (J. Med. Chem. 1999, 42, 3623-3628), a tyrosine, a tyrosine derivative, a lipid, a dehydroascorbic acid derivative, a N-acetylgalactosamine derivative, a glucose derivative, a galactose derivative, a mannose derivative, a fatty acid derivative, a natural peptide comprising of 2-13 amino acids, a modified peptide comprising of 2-13 amino acids, a sigma-2 receptor binding ligand derivative, a retinoic acid derivative, a prostate specific membrane antigen (PSMA) binding ligand derivative, a folic acid derivative, a glycirrhetinic acid (GA) receptor binding ligand derivative, an Asialo Glycoprotein Receptor (ASGPR) binding ligand derivative or a chemical derivative that allows selective uptake by a cell through a preferentially expressed receptor or transporter that exists on or exposed to the cell surface.

In some other embodiments, the present invention provides compounds of formula I″, and its corresponding pharmaceutically acceptable salts, compositions, prodrugs, dosage forms and CDN-ligand conjugates thereof.

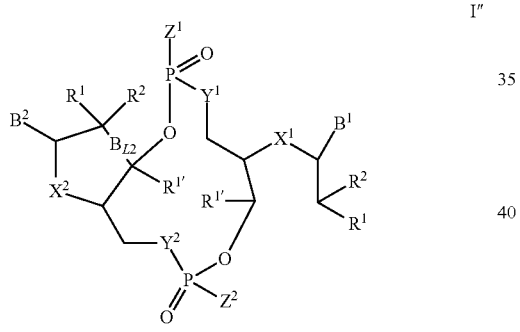

I″

Wherein:

B$^1$ and B$^2$ are independently and optionally selected from the group consisting of:

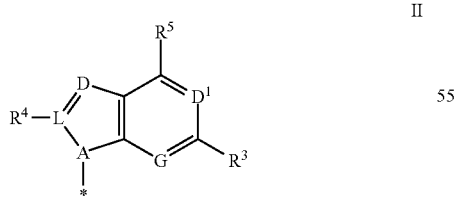

II

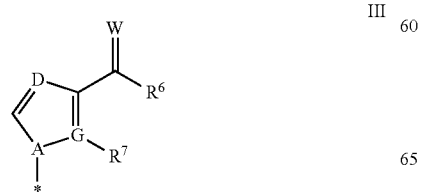

III

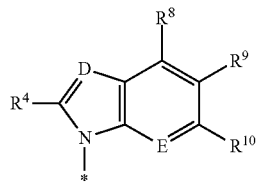

IV

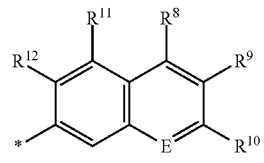

V

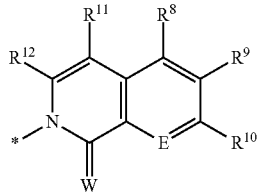

VI

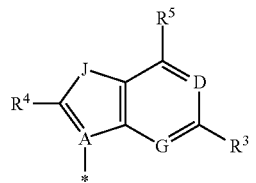

VII

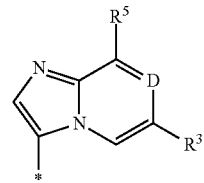

VIII

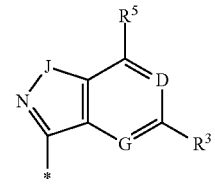

IX

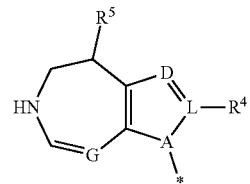

X

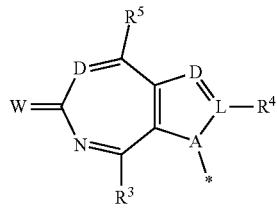

XI

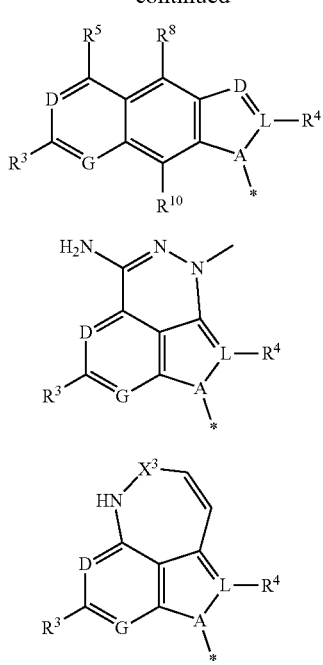

each $R^1$ and $R^2$ are independently and optionally selected from the group consisting of hydrogen, halogen, —$NO_2$, —CN, —OR, —SR, —NHR, —N(R)$_2$, —C(O)R, —$CO_2$R, —C(O)$CH_2$C(O)R, —S(O)R, —S(O)$_2$R, —C(O)N(R)$_2$, —$SO_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)$SO_2$N(R)$_2$, —N(R)$SO_2$R, —OC(O)N(R)$_2$, and optionally substituted $C_{1-12}$ aliphatic or $C_{1-4}$ alkoxy-$C_{1-4}$ alkyl;

$R^1$ and $R^2$ cannot be the same except for hydrogen.

$B_{L2}$ is a bond connecting the two carbons attached to it or optionally not a bond.

Each $R^{1'}$ are independently and optionally selected from a group consisting of hydrogen, halogen, $N_3$, C(O)OH, CN, C(O)$NH_2$, C(S)$NH_2$, C(O)OR or R.

Each $R^3$, $R^4$, $R^5$, $R^8$, $R^9$, $R^{10}$, $R^{11}$ and $R^{12}$ is independently and optionally selected from a group consisting of hydrogen, halogen, —$NO_2$, —CN, R, —OR, —SR, —NHR, —N(R)$_2$, —C(O)R, —$CO_2$R, —C(O)C(O)R, —C(O)$CH_2$C(O)R, —S(O)R, —S(O)$_2$R, —C(O)N(R)$_2$, —$SO_2$N(R)$_2$, —OC(O)R, —N(R)C(O)R, —N(R)C(=NR)N(R)$_2$, —C(=NR)N(R)$_2$, —C=NOR, —N(R)$SO_2$N(R)$_2$, —N(R)$SO_2$R, —OC(O)N(R)$_2$, or an optionally substituted group selected from $C_{1-12}$ aliphatic, phenyl, a 3-6 membered saturated or partially unsaturated monocyclic carbocyclic ring, a 3-6 membered saturated or partially unsaturated heterocyclic ring having 1-2 heteroatoms independently selected from nitrogen, oxygen, or sulfur, and a 5-6 membered heteroaryl ring having 1-3 heteroatoms independently selected from nitrogen, oxygen, or sulfur.

$R^6$ is independently $NH_2$, NHR, OH, —OR, —SR, —N(R)$_2$ $R^7$ is independently halogen, $NH_2$, NHR, OH, OR, SH, SR, —N(R)$_2$ when G is a C, and $R^7$ is absent when G is N.

Each R is independently selected from the group consisting of hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, and a 5-6 membered heteroaryl ring having 1-3 heteroatoms independently selected from nitrogen, oxygen, or sulfur; or: two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur.

A, E and G are independently N, C, $CR^a$ where $R^a$ is independently halogen or H.

D is independently selected from N, CH, C—CN, C—$NO_2$, CR, C—$NH_2$, C—NHR, CN(R)$_2$, CF, Cl, C—CONH$_2$, C—CONHR, C—CON(R)$_2$, C—CSN(R)$_2$, C—COOR, C—C(=NH)$NH_2$, C—OH, C—OR, C—$C_{1-4}$ alkylamino, C-di($C_{1-4}$ alkyl)amino, C-(1,3-oxazol-2-yl), C-(1,3-thiazol-2-yl), or C-(imidazol-2-yl); Wherein alkyl is optionally substituted with one to three groups independently selected from halogen, amino, hydroxyl, carboxyl, or $C_{1-3}$ alkoxy.

$D^1$ is independently selected from N, CH, C—CN, C—$NO_2$, CR, C—$NH_2$, C—NHR, CN(R)$_2$, CF, Cl, C—CONH$_2$, C—CONHR, C—CON(R)$_2$, C—CSN(R)$_2$, C—COOR, C—C(=NH)$NH_2$, C—OH, C—OR, C—$C_{1-4}$ alkylamino, C-di($C_{1-4}$ alkyl)amino, C-(1,3-oxazol-2-yl), C-(1,3-thiazol-2-yl), or C-(imidazol-2-yl); Wherein alkyl is optionally substituted with one to three groups independently selected from halogen, amino, hydroxyl, carboxyl, or $C_{1-3}$ alkoxy.

J is independently selected from O, S, $SO_2$, NH or NR.

In structure II, L is independently selected from C or N; wherein when L is N, $R^4$ is absent and when L is C, $R^4$ is as defined above.

W is independently O, S or NH.

$X^1$ and $X^2$ are independently and optionally for each occurrence an O, S, NH, NR, $CH_2$, CHR, C(R)$_2$, C=$CH_2$, or C=$CF_2$.

$X^3$ may independently and optionally be selected from, O, NH, C=O, $SO_2$, C=NH, NR $Y^1$ and $Y^2$ is independently and optionally for each occurrence an O, S, NH, $CH_2$, $CF_2$ or $CCl_2$ $Z^1$ and $Z^2$ are independently selected from: O$^-$, S$^-$, OH, SH, H, $CH_3$, F, $BH_3^-$. It can be appreciated that the negative charges are balanced by positive counter ions to form pharmaceutically acceptable salts.

Alternatively, $Z^1$ and $Z^2$ are independently selected from O$L^2$, $OCH_2CH_2L^2$, $OCH_2OC(O)L^2$, $OCH_2OC(O)NHL^2$, $OCH_2OC(O)N(L^2)_2$, $OCH_2OC(O)OL^2$, $OCH_2OC(O)SL^2$, $OCH_2NHC(O)L^2$, $OCH_2SC(O)L^2$, $OCH_2(CH_2)_{1-6}OC(O)L^2$, $OCH_2(CH_2)_{1-6}SC(O)L^2$, $OCH_2(CH_2)_{1-6}NHC(O)L^2$, $OCH_2(CH_2)_{1-6}OC(O)OL^2$, $OCH_2(CH_2)_{1-6}SC(O)OL^2$, $OCH_2(CH_2)_{1-6}NHC(O)OL^2$, $OCH_2O(CO)C(CH_3)_3$, $OCH_2O(CO)C(CH_3)_2CH_2OL^2$, $OCH_2S(CO)C(CH_3)_2CH_2OL^2$, $OCH_2CH_2O(CO)C(CH_3)_3$, $OCH_2CH_2S(CO)C(CH_3)_3$, $OCH_2CH_2O(CO)C(CH_3)_2CH_2OL^2$, $OCH_2CH_2S(CO)C(CH_3)_2CH_2OL^2$, $OCH_2CH_2S$—$SCH_2(CH_2)_{0-6}L^2$, $OCH_2CH_2S$—$SCH_2(CH_2)_{0-6}OL^2$, —$O(CH_2CH_2O)_{2-20}L^2$, —$O(CH_2CH_2O)_{2-20}$ C(O)$OL^2$, —$O(CH_2CH_2O)_{2-20}$ C(O)$NHL^2$, —$O(CH_2CH_2O)_{2-20}$ $CH_2CH_2NHC(O)L^2$, —$O(CH_2CH_2O)_{2-20}$ C(O)N($L^2$)$_2$, —$S(CH_2CH_2O)_{2-20}L^2$, —$S(CH_2CH_2O)_{2-20}$ C(O)$OL^2$, —$S(CH_2CH_2O)_{2-20}$ C(O)$NHL^2$, —$S(CH_2CH_2O)_{2-20}$ C(O)N($L^2$)$_2$.

Where $L^2$ is independently and optionally selected from any of the following: H, $N_3$, $C_{1-20}$ straight chain alkyl, a $C_{1-20}$ straight chain alkenyl, $C_{1-20}$ alkynyl, $C_{3-6}$ cycloalkyl, $C_{1-6}$ haloalkyl, a tert-butyl, a substituted tert-butyl, a glucuronide moiety, (J. Med. Chem. 1999, 42, 3623-3628), a tyrosine, a tyrosine derivative, a lipid, a dehydroascorbic acid derivative, a N-acetylgalactosamine derivative, a glucose derivative, a galactose derivative, a mannose derivative, a fatty acid derivative, a natural peptide comprising of 2-13 amino acids, a modified peptide comprising of 2-13 amino acids, a sigma-2 receptor binding ligand derivative, a retinoic acid derivative, a prostate specific membrane antigen (PSMA) binding ligand derivative, a folic acid derivative, a glycirrhetinic acid (GA) receptor binding ligand derivative, an Asialo Glycoprotein Receptor (ASGPR) binding ligand derivative or a chemical derivative that allows selective uptake by a cell through a preferentially expressed receptor or transporter that exists on or exposed to the cell surface.

Synthesis of Cyclic Dinucleotides

Synthesis of cyclic dinucleotides embodied in this invention can be carried out by anyone who is skilled in the art of organic synthesis, specifically in the art of nucleoside and nucleotide synthesis, following literature procedure, amply available. For example, synthetic schemes available in Pascale Clivio, Stephanie Coantic-Castex, and Dominique Guillaume, Chemical Reviews, Chem. Rev. 2013, 113, 7354-7401 is given in its entirety as an example. Additionally, synthesis by Barbara L. Gaffney, Organic Letters, 2010 Jul. 16; 12(14): 3269-3271 2010, Barbara L. Gaffney and Roger A. Jones Curr Protoc Nucleic Acid Chem. 2012 March; CHAPTER: Unit 14.8, Xu Zhang et al., Molecular Cell 51, 226-235, Jul. 25, 2013 (supplementary material), Shi Min Ching et al., Bioorganic & Medicinal Chemistry 18 (2010) 6657-6665 may be used as examples for executing synthesis of CDN molecules of the current invention. For brevity, following general synthesis scheme is given as a general example. Many modifications and alteration of reagents can be used to manipulate this general scheme, by one who is skilled in the art, to obtain desired results in terms of analogues, improvement in yield, scale up from grams to kilogram scale, environmentally friendly synthesis and ease of synthesis.

For example, a typical phosphorothioate modified cyclic dinucleotide of the present invention can be prepared, by a person of the skilled art, by following the scheme outlined below.

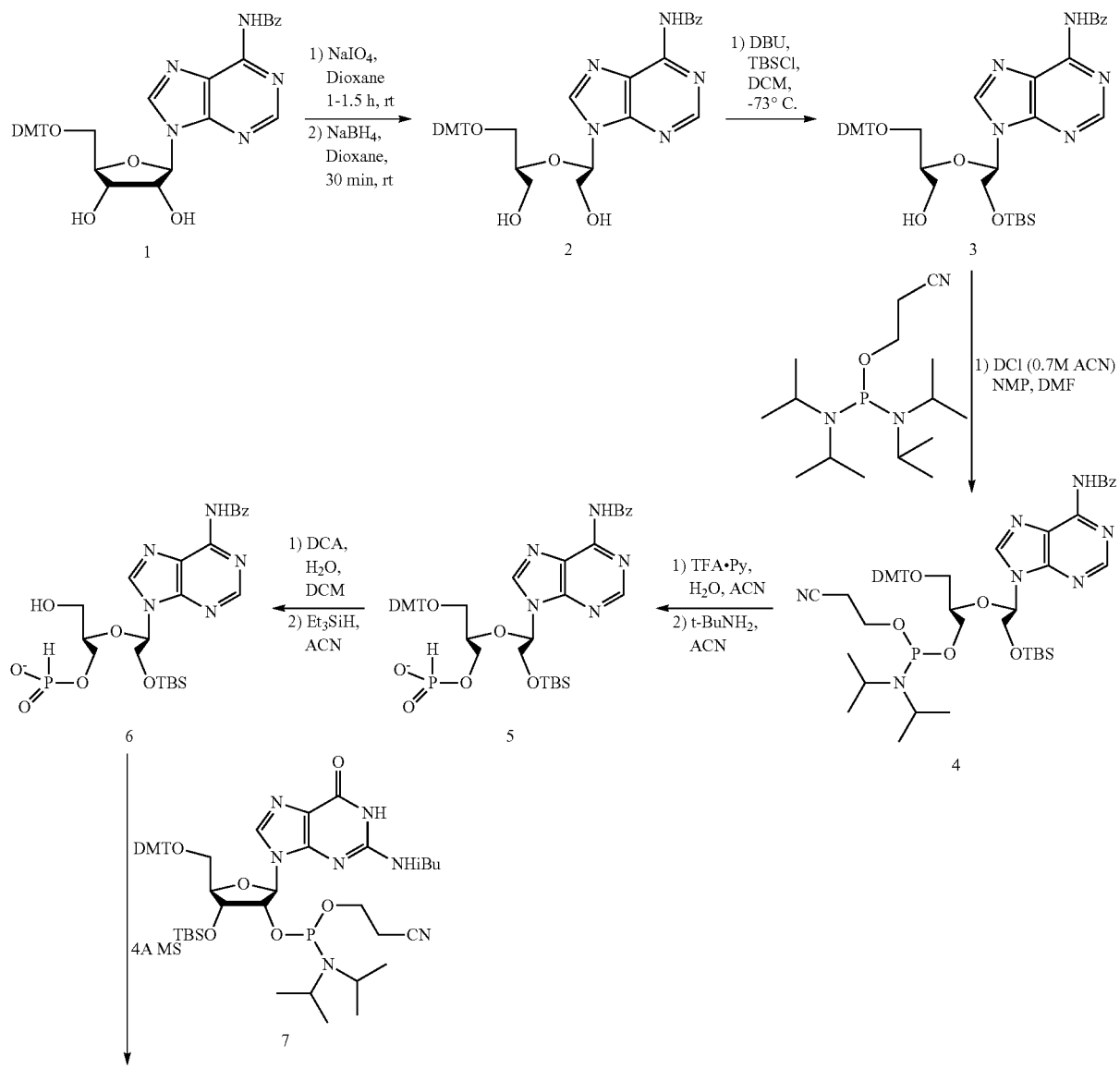

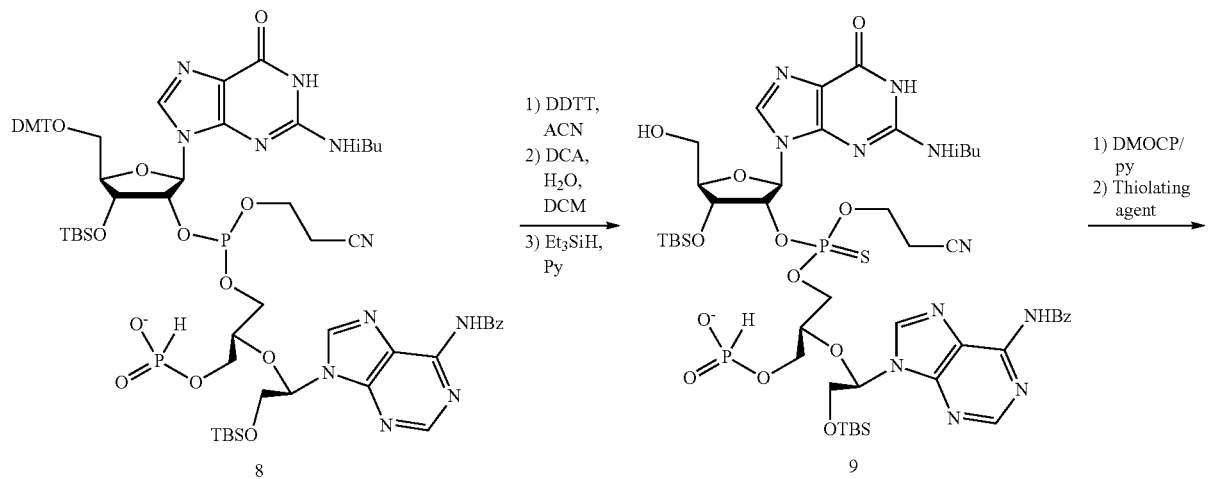
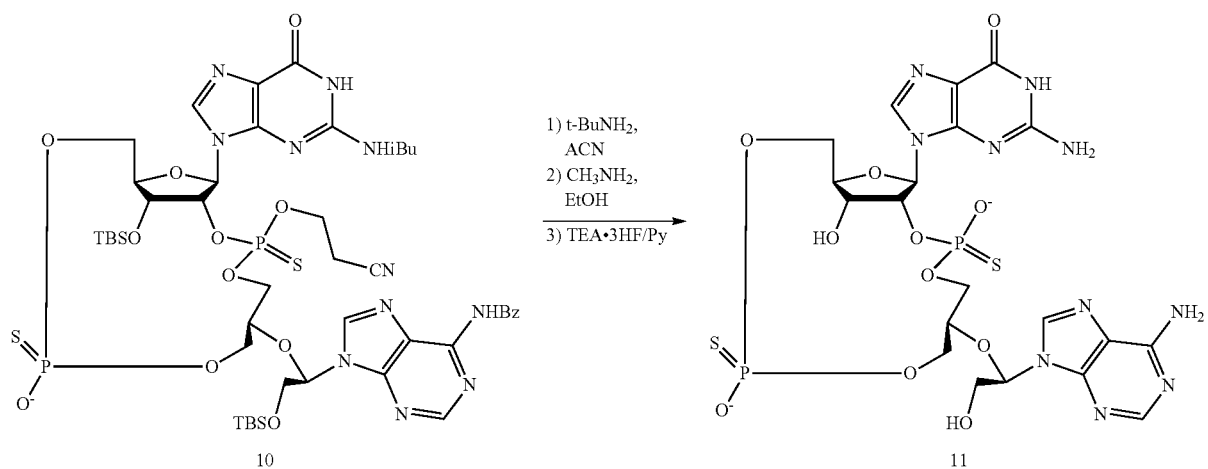
Yet, another cyclic dinucleotide of the present invention can be prepared, by a person skilled in the art, by following the scheme outlined below
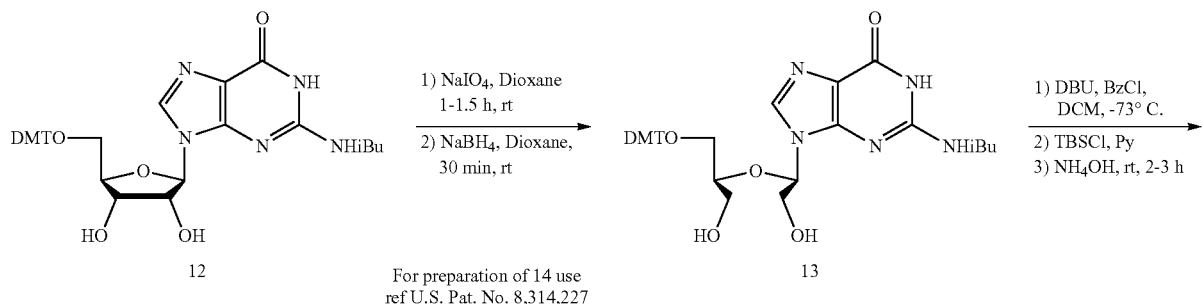
For preparation of 14 use
ref U.S. Pat. No. 8,314,227

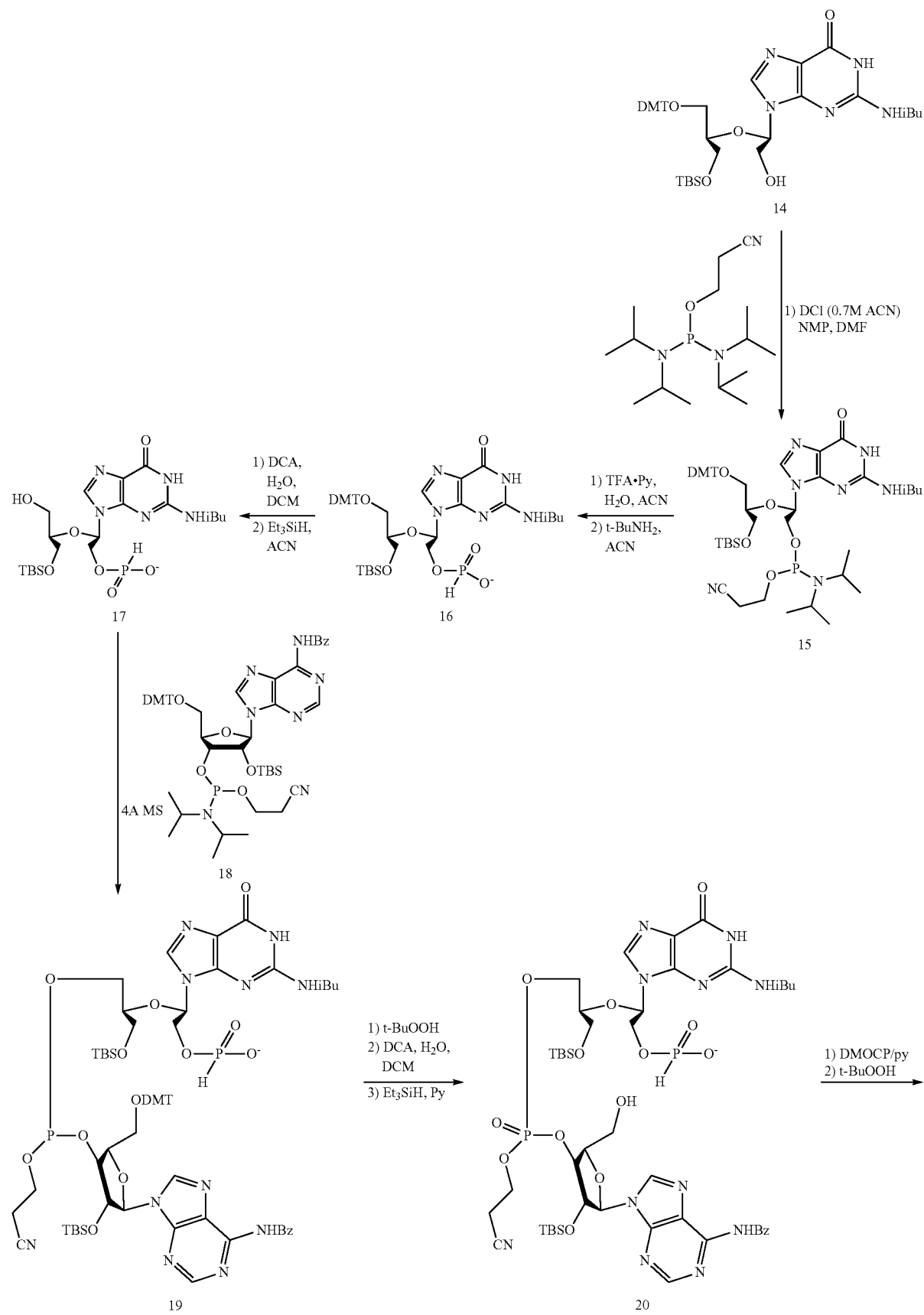

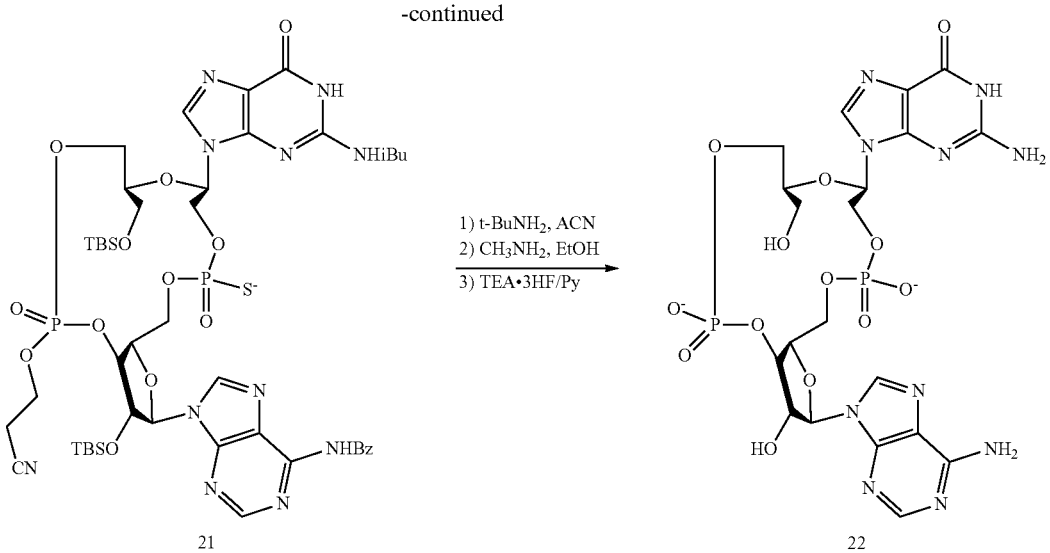

All the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods described herein without departing from the concept, spirit and scope of the invention. Such variations are intended to fall within the scope of the appended claims.

What is claimed is:

1. A compound of formula I

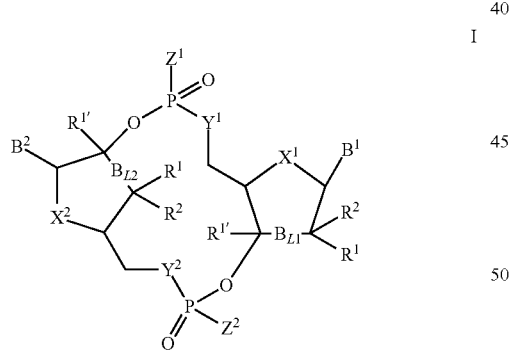

I wherein, $B^1$ and $B^2$ are selected from a group consisting of

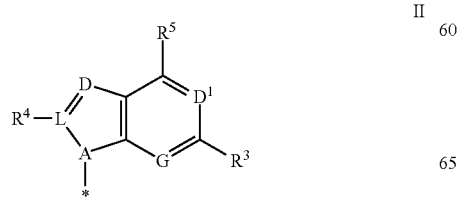

II

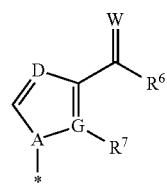

III

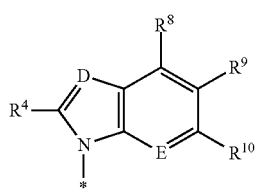

IV

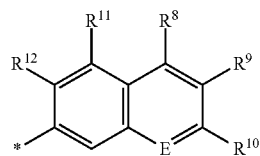

V

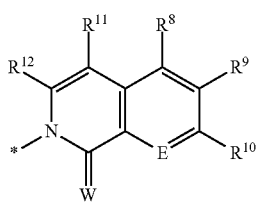

VI

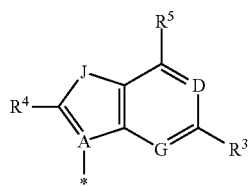

VII

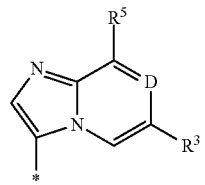

VIII

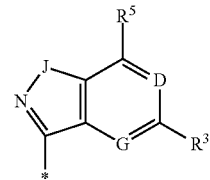

IX

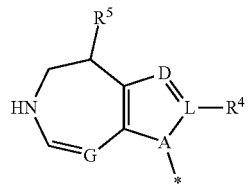

X

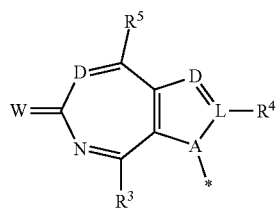

XI

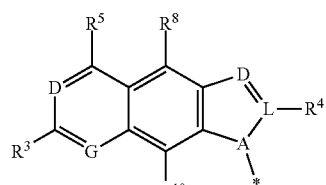

XII

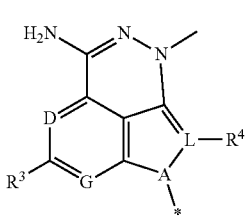

XIII

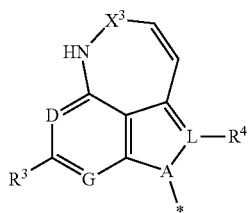

XIV

Wherein, each $R^3$, $R^4$, $R^5$, $R^8$, $R^9$, $R^{10}$, $R^{11}$ and $R^{12}$ is selected from a group consisting of hydrogen, halogen, —NO₂, —CN, R, —OR, —SR, —NHR, —N(R)₂, —C(O)R, —CO₂R, —C(O)C(O)R, —C(O)CH₂C(O)R, —S(O)R, —S(O)₂R, —C(O)N(R)₂, —SO₂N(R)₂, —OC(O)R, —N(R)C(O)R, —N(R)C(=NR)N(R)₂, —C(=NR)N(R)₂, —C=NOR, —N(R)SO₂N(R)₂, —N(R)SO₂R, —OC(O)N(R)₂, and $R^6$ is selected from a group consisting of NH₂, NHR, OH, —OR, —SR, —N(R)₂, $R^7$ is selected from a group consisting of NH₂, NHR, OH, OR, SH, SR, —N(R)₂ when G is a C, and $R^7$ is absent when G is N, Each R is independently selected from a group consisting of hydrogen, $C_{1-6}$ aliphatic, phenyl, a 3-7 membered saturated, partially unsaturated carbocyclic ring, A, E and G are selected from a group consisting of N, C, $CR^a$ where $R^a$ is independently a halogen or H, D is selected from a group consisting of N, CH, C—CN, C—NO₂, CR, C—NH₂, C—NHR, CN(R)₂, CF, Cl, C—CONH₂, C—CONHR, C—CON(R)₂, C—CSN(R)₂, C—COOR, C—C(=NH)NH₂, C—OH, C—OR, C—$C_{1-4}$ alkylamino, C-di($C_{1-4}$ alkyl)amino, C-(1,3-oxazol-2-yl), C-(1,3-thiazol-2-yl), or C-(imidazol-2-yl); wherein alkyl is optionally substituted with one to three groups selected from a group consisting of halogen, amino, hydroxyl, carboxyl, or $C_{1-3}$ alkoxy, $D^1$ is selected from a group consisting of N, CH, C—CN, C—NO₂, CR, C—NH₂, C—NHR, CN(R)₂, CF, Cl, C—CONH₂, C—CONHR, C—CON(R)₂, C—CSN(R)₂, C—COOR, C—C(=NH)NH₂, C—OH, C—OR, C—$C_{1-4}$ alkylamino, C-di($C_{1-4}$ alkyl)amino, C-(1,3-oxazol-2-yl), C-(1,3-thiazol-2-yl), or C-(imidazol-2-yl); wherein alkyl is optionally substituted with one to three groups independently selected from a group consisting of halogen, amino, hydroxyl, carboxyl, $C_{1-3}$ alkoxy, J is selected from a group consisting of O, S, SO₂, NH, NR, L is selected from a group consisting of C, N; wherein when L is N, $R^4$ is absent and when L is C, $R^4$ is as defined above, W is selected from a group consisting of O, S, NH, $R^1$ and $R^2$ are independently and optionally selected from a group consisting of hydrogen, halogen, —NO₂, —CN, —OR, —SR, —NHR, —N(R)₂, —C(O)R, —CO₂R, —C(O)CH₂C(O)R, —S(O)R, —S(O)₂R, —C(O)N(R)₂, —SO₂N(R)₂, —OC(O)R, —N(R)C(O)R, —N(R)N(R)₂, —N(R)C(=NR)N(R)₂, —C(=NR)N(R)₂, —C=NOR, —N(R)C(O)N(R)₂, —N(R)SO₂N(R)₂, —N(R)SO₂R, —OC(O)N(R)₂, and optionally substituted $C_{1-12}$ aliphatic or $C_{1-4}$ alkoxy-$C_{1-4}$ alkyl;

$R^1$ and $R^2$ cannot be the same except for hydrogen,

Either $B_{L1}$ or $B_{L2}$ is independently and optionally a bond connecting the two carbons attached to each of them, Either $B_{L1}$ or $B_{L2}$ are independently absent or both $B_{L1}$ and $B_{L2}$ may be absent such that no C—C bond exists, Both $B_{L1}$ and $B_{L2}$ cannot be a bond at the same time, Each $R^{1'}$ is selected from a group consisting of hydrogen, halogen, N₃, C(O)OH, CN, C(O)NH₂, C(S)NH₂, C(O)OR, R, $X^1$ and $X^2$ are selected from a group consisting of O, S, NH, NR, CH₂, CHR, C(R)₂, C=CH₂, C=CF₂, $X^3$ is selected from a group consisting of O, NH, C=O, SO₂, C=NH, NR, $Y^1$ and $Y^2$ are selected from a group consisting of O, S, NH, CH₂, CF₂ or CCl₂

$Z^1$ and $Z^2$ are selected from a group consisting of O⁻, S⁻, OH, SH, H, CH₃, F, BH₃⁻, Alternatively, $Z^1$ and $Z^2$ are selected from a group consisting of $OL^2$, $OCH_2CH_2L^2$, $OCH_2OC(O)L^2$, $OCH_2OC(O)NHL^2$, $OCH_2OC(O)N(L^2)_2$, $OCH_2OC(O)$ $OL^2$, $OCH_2OC(O)SL^2$, $OCH_2NHC(O)L^2$, $OCH_2SC(O)L^2$, $OCH_2(CH_2)_{1-6}OC(O)L^2$, $OCH_2(CH_2)_{1-6}SC(O)$ L², OCH₂(CH₂)₁₋₆NHC(O)L², OCH₂(CH₂)₁₋₆OC(O)OL², OCH₂(CH₂)₁₋₆SC(O)OL², OCH₂(CH₂)₁₋₆NHC(O)OL², OCH₂O(CO)C(CH₃)₃, OCH₂O(CO)C(CH₃)₂CH₂OL², OCH₂S(CO)C(CH₃)₂CH₂OL², OCH₂CH₂O(CO)C(CH₃)₃, OCH₂CH₂S(CO)C(CH₃)₃, OCH₂ CH₂ O(CO)C(CH₃)₂CH₂OL², OCH₂ CH₂ S(CO)C(CH₃)₂CH₂OL², OCH₂CH₂S—SCH₂(CH₂)₀₋₆L², OCH₂CH₂S—SCH₂(CH₂)₀₋₆OL², —O(CH₂CH₂O)₂₋₂₀L², —O(CH₂CH₂O)₂₋₂₀ C(O)OL², —O(CH₂CH₂O)₂₋₂₀ C(O)NHL², —O(CH₂CH₂O)₂₋₂₀ CH₂CH₂NHC(O)L², —O(CH₂CH₂O)₂₋₂₀ C(O)N(L²)₂, —S(CH₂CH₂O)₂₋₂₀L², —S(CH₂CH₂O)₂₋₂₀ C(O)OL², —S(CH₂CH₂O)₂₋₂₀ C(O)NHL², —S(CH₂CH₂O)₂₋₂₀ C(O)N(L²)₂, where L² is independently selected from a group consisting of H, N₃, C₁₋₂₀ straight chain alkyl, a C₁₋₂₀ straight chain alkenyl, C₁₋₂₀ alkynyl, C₃₋₆ cycloalkyl, C₁₋₆ haloalkyl, a tert-butyl, a substituted tert-butyl, a glucuronide moiety, a tyrosine.

2. The compound according to claim 1, wherein, B¹ and B² are independently selected from a group consisting of,

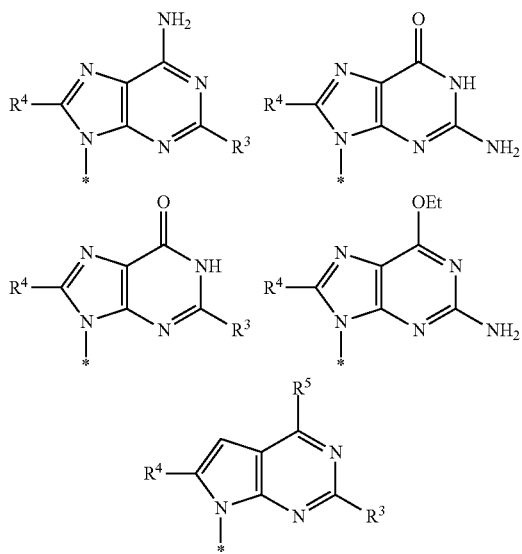

wherein, each R³, R⁴ and R⁵ are independently and optionally selected from a group consisting of hydrogen, halogen, —NO₂, —CN, R, —OR, —SR, —NHR, —N(R)₂, —C(O)R, —CO₂R, —C(O)C(O)R, —C(O)CH₂C(O)R, —S(O)R, —S(O)₂R, —C(O)N(R)₂, —SO₂N(R)₂, —OC(O)R, —N(R)C(O)R, —N(R)C(=NR)N(R)₂, —C(=NR)N(R)₂, —C=NOR, —N(R)SO₂N(R)2, —N(R)SO₂R, —OC(O)N(R)₂, C₁₋₁₂ aliphatic, phenyl, each R is independently selected from the group consisting of hydrogen, C₁₋₆ aliphatic, phenyl, R¹ and R² are independently and optionally selected from the group consisting of hydrogen, halogen, OH, —NO₂, —CN, —OR, —SR, —NHR, —N(R)₂, —C(O)R, —CO₂R, —C(O)CH₂C(O)R, —S(O)R, —S(O)₂R, —C(O)N(R)₂, —SO₂N(R)₂, —OC(O)R, —N(R)C(O)R, —N(R)N(R)₂, —N(R)C(=NR)N(R)₂, —C(=NR)N(R)₂, —C=NOR, —N(R)C(O)N(R)₂, —N(R)SO₂N(R)₂, —N(R)SO₂R, —OC(O)N(R)₂, optionally substituted C₁₋₁₂ aliphatic, C₁₋₄ alkoxy, —C₁₋₄ alkyl;

R¹ and R² cannot be the same except for hydrogen, either B_{L1} or B_{L2} is independently and optionally a bond connecting the two carbons attached to each of them, either B_{L1} or B_{L2} may be optionally absent or both B_{L1} and B_{L2} may be absent such that no C—C bond exists, both B_{L1} and B_{L2} cannot be a bond at the same time, each R¹ is independently and optionally selected from a group consisting of hydrogen, halogen, OH, N₃, C(O)OH, CN, C(O)NH₂, C(S)NH₂, C(O)OR, R, X¹ and X² are selected from a group consisting of O, S, NH, NR, CH₂, CHR, C(R)₂, C=CH₂, C=CF₂

Y¹ and Y² are selected from a group consisting of O, S, NH, CH₂, CF₂, CCl₂,

Z¹ and Z² are selected from a group consisting of O⁻, S⁻, OH, SH, H, CH₃, F, BH₃⁻, alternatively, Z¹ and Z² are selected from a group consisting of OL², OCH₂CH₂L², OCH₂OC(O)L², OCH₂OC(O)NHL², OCH₂OC(O)N(L²)₂, OCH₂OC(O)OL², OCH₂OC(O)SL², OCH₂NHC(O)L², OCH₂SC(O)L², OCH₂(CH₂)₁₋₆OC(O)L², OCH₂(CH₂)₁₋₆SC(O)L², OCH₂(CH₂)₁₋₆NHC(O)L², OCH₂(CH₂)₁₋₆OC(O)OL², OCH₂(CH₂)₁₋₆SC(O)OL², OCH₂(CH₂)₁₋₆NHC(O)OL², OCH₂O(CO)C(CH₃)₃, OCH₂O(CO)C(CH₃)₂CH₂OL², OCH₂S(CO)C(CH₃)₂CH₂OL², OCH₂CH₂O(CO)C(CH₃)₃, OCH₂CH₂S(CO)C(CH₃)₃, OCH₂ CH₂ O(CO)C(CH₃)₂CH₂OL², OCH₂ CH₂ S(CO)C(CH₃)₂CH₂OL², OCH₂CH₂S—SCH₂(CH₂)₀₋₆L², OCH₂CH₂S—SCH₂(CH₂)₀₋₆OL², —O(CH₂CH₂O)₂₋₂₀L², —O(CH₂CH₂O)₂₋₂₀ C(O)OL², —O(CH₂CH₂O)₂₋₂₀ C(O)NHL², —O(CH₂CH₂O)₂₋₂₀ CH₂CH₂NHC(O)L², —O(CH₂CH₂O)₂₋₂₀ C(O)N(L²)₂, —S(CH₂CH₂O)₂₋₂₀L², —S(CH₂CH₂O)₂₋₂₀ C(O)OL², —S(CH₂CH₂O)₂₋₂₀ C(O)NHL², —S(CH₂CH₂O)₂₋₂₀ C(O)N(L²)₂, where L² is independently selected from a group consisting of H, N₃, C₁₋₂₀ straight chain alkyl, a C₁₋₂₀ straight chain alkenyl, C₁₋₂₀ alkynyl, C₃₋₆ cycloalkyl, C₁₋₆ haloalkyl, a tert-butyl, a substituted tert-butyl, a tyrosine.

3. The compound according to claim 1, wherein the compound of formula I is a compound of formula I(a),

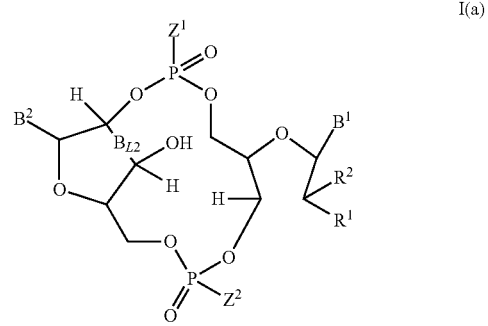

I(a)

wherein, B¹ and B² are independently selected from a group consisting of

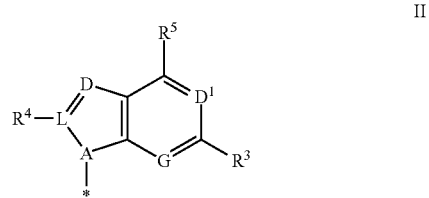

II

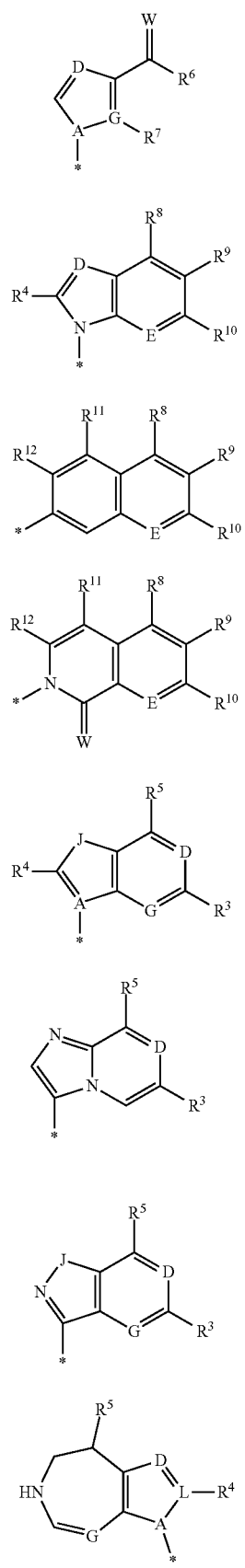

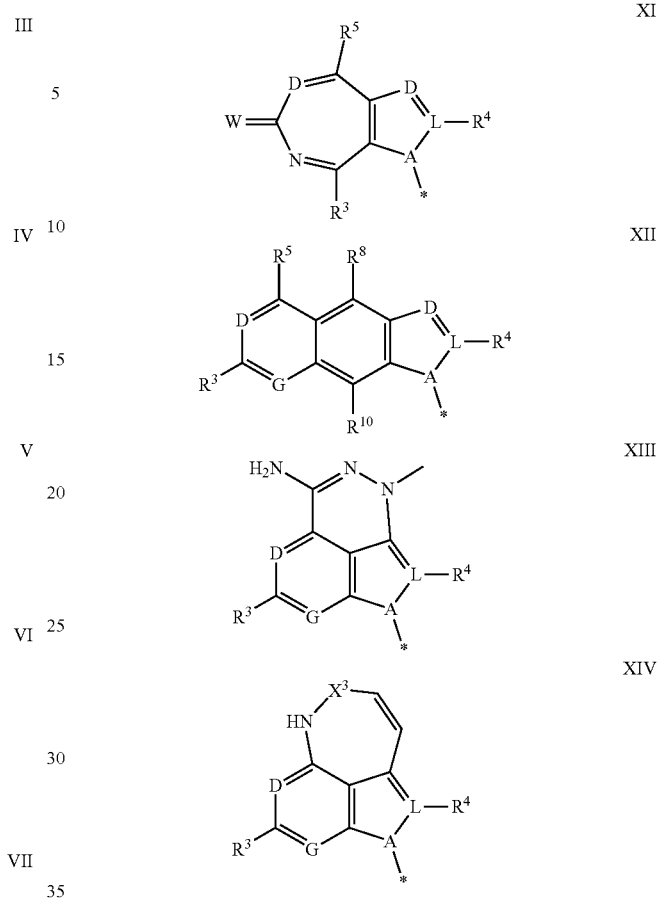

wherein, each $R^3$, $R^4$, $R^5$, $R^8$, $R^9$, $R^{10}$, $R^{11}$ and $R^{12}$ is independently and optionally selected from a group consisting of hydrogen, halogen, —$NO_2$, —CN, R, —OR, —SR, —NHR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)C(=NR)N(R)$_2$, —C(=NR)N(R)$_2$, —C=NOR, —N(R)SO$_2$N(R)$_2$, —N(R)SO$_2$R, —OC(O)N(R)$_2$, C$_{1-12}$ aliphatic, phenyl, $R^6$ is selected from a group consisting of NH$_2$, NHR, OH, —OR, —SR, —N(R)$_2$, $R^7$ is selected from a group consisting of halogen, NH$_2$, NHR, OH, OR, SH, SR, —N(R)$_2$ when G is a C, and $R^7$ is absent when G is N, each R is independently selected from the group consisting of hydrogen, C$_{1-6}$ aliphatic, phenyl, A, E and G are selected from a group consisting of N, C, CR$^a$ where R$^a$ is independently a halogen or H, D is selected from a group consisting of N, CH, C—CN, C—NO$_2$, CR, C—NH$_2$, C—NHR, CN(R)$_2$, CF, Cl, C—CONH$_2$, C—CONHR, C—CON(R)$_2$, C—CSN(R)$_2$, C—COOR, C—C(=NH)NH$_2$, C—OH, C—OR, C—C$_{1-4}$ alkylamino, C-di(C$_{1-4}$ alkyl)amino, C-(1,3-oxazol-2-yl), C-(1,3-thiazol-2-yl), C-(imidazol-2-yl);

D$^1$ is selected from a group consisting of N, CH, C—CN, C—NO$_2$, CR, C—NH$_2$, C—NHR, CN(R)$_2$, CF, Cl, C—CONH$_2$, C—CONHR, C—CON(R)$_2$, C—CSN(R)$_2$, C—COOR, C—C(=NH)NH$_2$, C—OH, C—OR, C—C$_{1-4}$ alkylamino, C-di(C$_{1-4}$ alkyl)amino, C-(1,3-oxazol-2-yl), C-(1,3-thiazol-2-yl), C-(imidazol-2-yl);

J is selected from a group consisting of O, S, SO$_2$, NH, NR,

L is selected from a group consisting of C, N; wherein when L is N, R$^4$ is absent and when L is C, R$^4$ is as defined above, W is independently selected from a group consisting of O, S, NH, R$^1$ and R$^2$ are independently and optionally selected from a group consisting of hydrogen, halogen, OH, —NO$_2$, —CN, —OR, —SR, —NHR, —N(R)$_2$, —C(O)R, —CO$_2$R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, C$_{1-12}$ aliphatic, C$_{1-4}$ alkoxy-C$_{1-4}$ alkyl, R$^1$ and R$^2$ cannot be the same except for hydrogen, B$_{L2}$ is a bond connecting the two carbons attached to it or optionally not a bond, X$^3$ is selected from a group consisting of O, NH, C=O, SO$_2$, C=NH, NR, Z$^1$ and Z$^2$ are selected from a group consisting of O$^-$, S$^-$, OH, SH, H, CH$_3$, F, BH$_3^-$, Alternatively, Z$^1$ and Z$^2$ are selected from a group consisting of OL$^2$, OCH$_2$CH$_2$L$^2$, OCH$_2$OC(O)L$^2$, OCH$_2$OC(O)NHL$^2$, OCH$_2$OC(O)N(L$^2$)$_2$, OCH$_2$OC(O)OL$^2$, OCH$_2$OC(O)SL$^2$, OCH$_2$NHC(O)L$^2$, OCH$_2$SC(O)L$^2$, OCH$_2$(CH$_2$)$_{1-6}$OC(O)L$^2$, OCH$_2$(CH$_2$)$_{1-6}$SC(O)L$^2$, OCH$_2$(CH$_2$)$_{1-6}$NHC(O)L$^2$, OCH$_2$(CH$_2$)$_{1-6}$OC(O)OL$^2$, OCH$_2$(CH$_2$)$_{1-6}$SC(O)OL$^2$, OCH$_2$(CH$_2$)$_{1-6}$NHC(O)OL$^2$, OCH$_2$O(CO)C(CH$_3$)$_3$, OCH$_2$O(CO)C(CH$_3$)$_2$CH$_2$OL$^2$, OCH$_2$S(CO)C(CH$_3$)$_2$CH$_2$OL$^2$, OCH$_2$CH$_2$O(CO)C(CH$_3$)$_3$, OCH$_2$CH$_2$S(CO)C(CH$_3$)$_3$, OCH$_2$CH$_2$O(CO)C(CH$_3$)$_2$CH$_2$OL$^2$, OCH$_2$CH$_2$S(CO)C(CH$_3$)$_2$CH$_2$OL$^2$, OCH$_2$CH$_2$S—SCH$_2$(CH$_2$)$_{0-6}$L$^2$, OCH$_2$CH$_2$S—SCH$_2$(CH$_2$)$_{0-6}$OL$^2$, —O(CH$_2$CH$_2$O)$_{2-20}$L$^2$, —O(CH$_2$CH$_2$O)$_{2-20}$ C(O)OL$^2$, —O(CH$_2$CH$_2$O)$_{2-20}$ C(O)NHL$^2$, —O(CH$_2$CH$_2$O)$_{2-20}$ CH$_2$CH$_2$NHC(O)L$^2$, —O(CH$_2$CH$_2$O)$_{2-20}$ C(O)N(L$^2$)$_2$, —S(CH$_2$CH$_2$O)$_{2-20}$L$^2$, —S(CH$_2$CH$_2$O)$_{2-20}$ C(O)OL$^2$, —S(CH$_2$CH$_2$O)$_{2-20}$ C(O)NHL$^2$, —S(CH$_2$CH$_2$O)$_{2-20}$, C(O)N(L$^2$)$_2$, where L$^2$ is independently and optionally selected from a group consisting of H, N$_3$, C$_{1-20}$ straight chain alkyl, a C$_{1-20}$ straight chain alkenyl, C$_{1-20}$ alkynyl, C$_{3-6}$ cycloalkyl, C$_{1-6}$ haloalkyl, a tert-butyl, a substituted tert-butyl, a tyrosine.

4. The compound according to claim 1, wherein the compound of formula I is a compound of formula I(b),

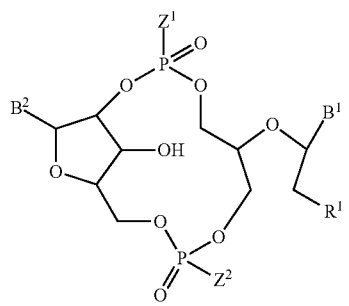

I(b)

wherein, B$^1$ and B$^2$ are independently selected from a group consisting of

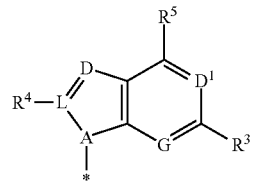

II

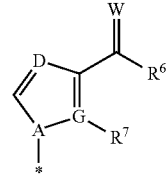

III

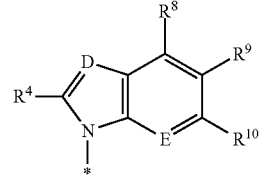

IV

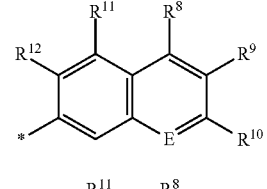

V

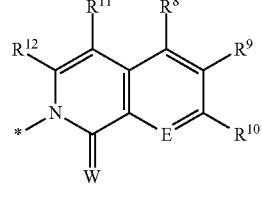

VI

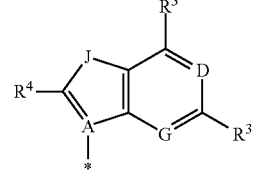

VII

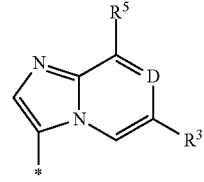

VIII

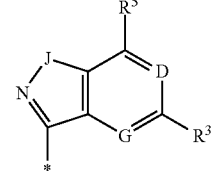

IX

-continued

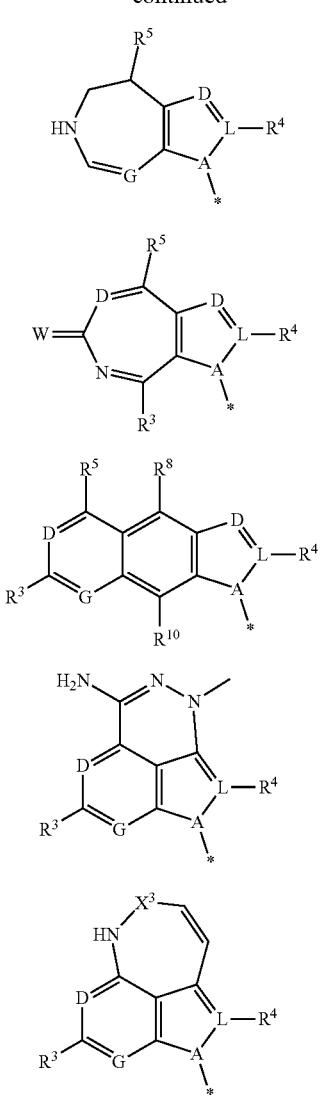

X

XI

XII

XIII

XIV wherein, each $R^3$, $R^4$, $R^5$, $R^8$, $R^9$, $R^{10}$, $R^{11}$ and $R^{12}$ is independently and optionally selected from a group consisting of hydrogen, halogen, —$NO_2$, —CN, R, —OR, —SR, —NHR, —$N(R)_2$, —C(O)R, —$CO_2R$, —C(O)C(O)R, —C(O)$CH_2$C(O)R, —S(O)R, —S(O)$_2$R, —C(O)$N(R)_2$, —$SO_2N(R)_2$, —OC(O)R, —N(R)C(O)R, —N(R)C(=NR)$N(R)_2$, —C(=NR)$N(R)_2$, —C=NOR, —N(R)$SO_2N(R)_2$, —N(R)$SO_2$R, —OC(O)$N(R)_2$, an optionally substituted group selected from $C_{1-12}$ aliphatic, phenyl, $R^6$ is selected from a group consisting of $NH_2$, NHR, OH, —OR, —SR, —$N(R)_2$, $R^7$ is selected from a group consisting of halogen, $NH_2$, NHR, OH, OR, SH, SR, —$N(R)_2$, when G is a C, and $R^7$ is absent when G is N, each R is independently selected from the group consisting of hydrogen, $C_{1-6}$ aliphatic, phenyl, A, E and G are selected from a group consisting of N, C, $CR^a$, where $R^a$ is independently a halogen or H, D is selected from a group consisting of N, CH, C—CN, C—$NO_2$, CR, C—$NH_2$, C—NHR, $CN(R)_2$, CF, Cl, C—$CONH_2$, C—CONHR, C—$CON(R)_2$, C—$CSN(R)_2$, C—COOR, C—C(=NH)$NH_2$, C—OH, C—OR, C—$C_{1-4}$ alkylamino, C-di($C_{1-4}$ alkyl)amino, C-(1,3-oxazol-2-yl), C-(1,3-thiazol-2-yl), C-(imidazol-2-yl), $D^1$ is selected from a group consisting of N, CH, C—CN, C—$NO_2$, CR, C—$NH_2$, C—NHR, $CN(R)_2$, CF, Cl, C—$CONH_2$, C—CONHR, C—$CON(R)_2$, C—$CSN(R)_2$, C—COOR, C—C(=NH)$NH_2$, C—OH, C—OR, C—$C_{1-4}$ alkylamino, C-di($C_{1-4}$ alkyl)amino, C-(1,3-oxazol-2-yl), C-(1,3-thiazol-2-yl), C-(imidazol-2-yl), J is selected from a group consisting of O, S, $SO_2$, NH, NR, L is selected from a group consisting of C, N; wherein when L is N, $R^4$ is absent and when L is C, $R^4$ is as defined above, W is selected from a group consisting of O, S, NH, $R^1$ is independently and optionally selected from the group consisting of hydrogen, halogen, OH, —$NO_2$, —CN, —OR, —SR, —NHR, —$N(R)_2$, —C(O)R, —$CO_2R$, —C(O)$CH_2$C(O)R, —S(O)R, —S(O)$_2$R, —C(O)$N(R)_2$, —$SO_2N(R)_2$, —OC(O)R, —N(R)C(O)R, —N(R)$N(R)_2$, —N(R)C(=NR)$N(R)_2$, —C(=NR)$N(R)_2$, —C=NOR, —N(R)C(O)$N(R)_2$, —N(R)$SO_2N(R)_2$, —N(R)$SO_2$R, —OC(O)$N(R)_2$, $C_{1-12}$ aliphatic or $C_{1-4}$ alkoxy-$C_{1-4}$ alkyl, $X^3$ is selected from a group consisting of O, NH, C=O, $SO_2$, C=NH, NR $Z^1$ and $Z^2$ are selected from a group consisting of $O^-$, $S^-$, OH, SH, H, $CH_3$, F, $BH_3^-$, alternatively, $Z^1$ and $Z^2$ are selected from a group consisting of $OL^2$, $OCH_2CH_2L^2$, $OCH_2OC(O)L^2$, $OCH_2OC(O)NHL^2$, $OCH_2OC(O)N(L^2)_2$, $OCH_2OC(O)OL^2$, $OCH_2OC(O)SL^2$, $OCH_2NHC(O)L^2$, $OCH_2SC(O)L^2$, $OCH_2(CH_2)_{1-6}OC(O)L^2$, $OCH_2(CH_2)_{1-6}SC(O)L^2$, $OCH_2(CH_2)_{1-6}NHC(O)L^2$, $OCH_2(CH_2)_{1-6}OC(O)OL^2$, $OCH_2(CH_2)_{1-6}SC(O)OL^2$, $OCH_2(CH_2)_{1-6}NHC(O)OL^2$, $OCH_2O(CO)C(CH_3)_3$, $OCH_2O(CO)C(CH_3)_2CH_2OL^2$, $OCH_2S(CO)C(CH_3)_2CH_2OL^2$, $OCH_2CH_2O(CO)C(CH_3)_3$, $OCH_2CH_2S(CO)C(CH_3)_3$, $OCH_2CH_2O(CO)C(CH_3)_2CH_2OL^2$, $OCH_2CH_2S(CO)C(CH_3)_2CH_2OL^2$, $OCH_2CH_2S—SCH_2(CH_2)_{0-6}L^2$, $OCH_2CH_2S—SCH_2(CH_2)_{0-6}OL^2$, —$O(CH_2CH_2O)_{2-20}L^2$, —$O(CH_2CH_2O)_{2-20}$ $C(O)OL^2$, —$O(CH_2CH_2O)_{2-20}$ $C(O)NHL^2$, —$O(CH_2CH_2O)_{2-20}$ $CH_2CH_2NHC(O)L^2$, —$O(CH_2CH_2O)_{2-20}$ $C(O)N(L^2)_2$, —$S(CH_2CH_2O)_{2-20}L^2$, —$S(CH_2CH_2O)_{2-20}$ $C(O)OL^2$, —$S(CH_2CH_2O)_{2-20}$ $C(O)NHL^2$, —$S(CH_2CH_2O)_{2-20}$ $C(O)N(L^2)_2$, where $L^2$ is independently and optionally selected from a group consisting of H, $N_3$, $C_{1-20}$ straight chain alkyl, a $C_{1-20}$ straight chain alkenyl, $C_{1-20}$ alkynyl, $C_{3-6}$ cycloalkyl, $C_{1-6}$ haloalkyl, a tert-butyl, a substituted tert-butyl, a tyrosine.

5. The compound according to claim 1, wherein the compound of formula I is a compound of formula I(c), (1c)

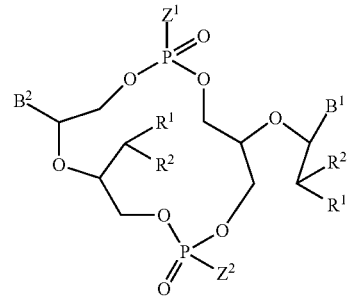

wherein, $B^1$ and $B^2$ are independently selected from a group consisting of

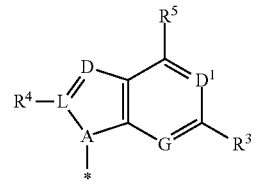

II

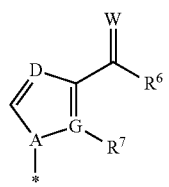

III

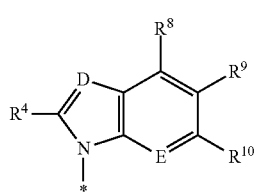

IV

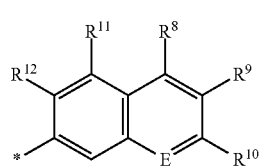

V

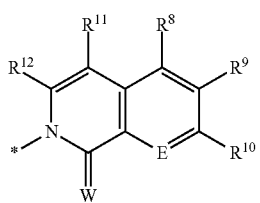

VI

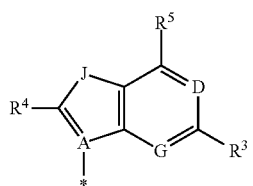

VII

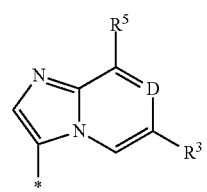

VIII

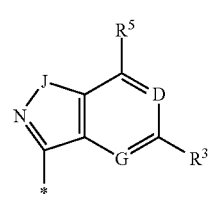

IX

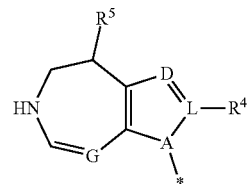

X

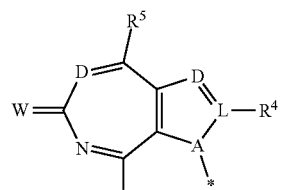

XI

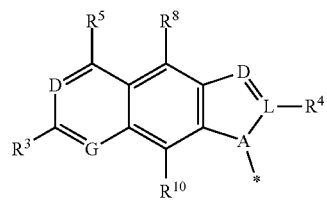

XII

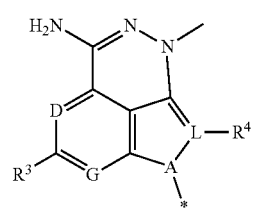

XIII

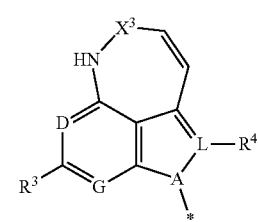

XIV wherein, each $R^3$, $R^4$, $R^5$, $R^8$, $R^9$, $R^{10}$, $R^{11}$ and $R^{12}$ is independently and optionally selected from a group consisting of hydrogen, halogen, —$NO_2$, —CN, R, —OR, —SR, —NHR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)C(=NR)N(R)$_2$, —C(=NR)N(R)$_2$, —C=NOR, —N(R)SO$_2$N(R)$_2$, —N(R)SO$_2$R, —OC(O)N(R)$_2$, $C_{1-12}$ aliphatic, phenyl, $R^6$ is independently NH$_2$, NHR, OH, —OR, —SR, —N(R)$_2$, $R^7$ is selected from a group consisting of NH$_2$, NHR, OH, OR, SH, SR, —N(R)$_2$ when G is a C, and $R^7$ is absent when G is N, each R is independently selected from the group consisting of hydrogen, $C_{1-6}$ aliphatic, phenyl, A, E and G are selected from a group consisting of N, C, CR$^a$ where R$^a$ is independently a halogen or H, D is selected from a group consisting of N, CH, C—CN, C—NO$_2$, CR, C—NH$_2$, C—NHR, CN(R)$_2$, CF, Cl, C—CONH$_2$, C—CONHR, C—CON(R)$_2$, C—CSN(R)$_2$, C—COOR, C—C(=NH)NH$_2$, C—OH, C—OR, C—$C_{1-4}$ alkylamino, C-di($C_{1-4}$ alkyl)amino, C-(1,3- oxazol-2-yl), C-(1,3-thiazol-2-yl), C-(imidazol-2-yl); wherein alkyl is optionally substituted with one to three groups selected from a group consisting of halogen, amino, hydroxyl, carboxyl, $C_{1-3}$ alkoxy, $D^1$ is selected from a group consisting of N, CH, C—CN, C—$NO_2$, CR, C—$NH_2$, C—NHR, $CN(R)_2$, CF, CI, C—$CONH_2$, C—CONHR, C—$CON(R)_2$, C—$CSN(R)_2$, C—COOR, C—C(=NH)$NH_2$, C—OH, C—OR, C—$C_{1-4}$ alkylamino, C-di($C_{1-4}$ alkyl)amino, C-(1,3-oxazol-2-yl), C-(1,3-thiazol-2-yl), C-(imidazol-2-yl), J is independently selected from a group consisting of O, S, $SO_2$, NH, NR, L is selected from a group consisting of C, N; wherein when L is N, $R^4$ is absent and when L is C, $R^4$ is as defined above, W is independently selected from a group consisting of O, S, NH, $R^1$ and $R^2$ are independently and optionally selected from a group consisting of hydrogen, halogen, OH, —$NO_2$, —CN, —OR, —SR, —NHR, —$N(R)_2$, —C(O)R, —$CO_2$R, —C(O)$CH_2$C(O)R, —S(O)R, —$S(O)_2$R, —C(O)$N(R)_2$, —$SO_2N(R)_2$, —OC(O)R, —N(R)C(O)R, —$N(R)N(R)_2$, —N(R)C(=NR)$N(R)_2$, —C(=NR)$N(R)_2$, —C=NOR, —N(R)C(O)$N(R)_2$, —N(R)$SO_2$$N(R)_2$, —N(R)$SO_2$R, —OC(O)$N(R)_2$, and optionally substituted with $C_{1-12}$ aliphatic or $C_{1-4}$ alkoxy-$C_{1-4}$ alkyl, $R^1$ and $R^2$ cannot be the same except for hydrogen, $X^3$ is selected from a group consisting of O, NH, C=O, $SO_2$, C=NH, NR, $Z^1$ and $Z^2$ are selected from a group consisting of $O^-$, $S^-$, OH, SH, H, $CH_3$, F, $BH_3^-$, Alternatively, $Z^1$ and $Z^2$ are selected from a group consisting of $OL^2$, $OCH_2CH_2L^2$, $OCH_2OC(O)L^2$, $OCH_2OC(O)NHL^2$, $OCH_2OC(O)N(L^2)_2$, $OCH_2OC(O)OL^2$, $OCH_2OC(O)SL^2$, $OCH_2NHC(O)L^2$, $OCH_2SC(O)L^2$, $OCH_2(CH_2)_{1-6}OC(O)L^2$, $OCH_2(CH_2)_{1-6}SC(O)L^2$, $OCH_2(CH_2)_{1-6}NHC(O)L^2$, $OCH_2(CH_2)_{1-6}OC(O)OL^2$, $OCH_2(CH_2)_{1-6}SC(O)OL^2$, $OCH_2(CH_2)_{1-6}NHC(O)OL^2$, $OCH_2O(CO)C(CH_3)_3$, $OCH_2O(CO)C(CH_3)_2CH_2OL^2$, $OCH_2S(CO)C(CH_3)_2CH_2OL^2$, $OCH_2CH_2O(CO)C(CH_3)_3$, $OCH_2CH_2S(CO)C(CH_3)_3$, $OCH_2CH_2O(CO)C(CH_3)_2CH_2OL^2$, $OCH_2CH_2S(CO)C(CH_3)_2CH_2OL^2$, $OCH_2CH_2S$—$SCH_2(CH_2)_{0-6}L^2$, $OCH_2CH_2S$—$SCH_2(CH_2)_{0-6}OL^2$, —$O(CH_2CH_2O)_{2-20}L^2$, —$O(CH_2CH_2O)_{2-20}C(O)OL^2$, —$O(CH_2CH_2O)_{2-20}C(O)NHL^2$, —$O(CH_2CH_2O)_{2-20}CH_2CH_2NHC(O)L^2$, —$O(CH_2CH_2O)_{2-20}C(O)N(L^2)_2$, —$S(CH_2CH_2O)_{2-20}L^2$, —$S(CH_2CH_2O)_{2-20}C(O)OL^2$, —$S(CH_2CH_2O)_{2-20}C(O)NHL^2$, —$S(CH_2CH_2O)_{2-20}C(O)N(L^2)_2$, where $L^2$ is independently and optionally selected from a group consisting of H, $N_3$, $C_{1-20}$ straight chain alkyl, a $C_{1-20}$ straight chain alkenyl, $C_{1-20}$ alkynyl, $C_{3-6}$ cycloalkyl, $C_{1-6}$ haloalkyl, a tert-butyl, a substituted tert-butyl, a glucuronide moiety, a tyrosine.

6. A pharmaceutical composition, said pharmaceutical composition comprising:
   a. the compound according to claim 1,
   b. A pharmaceutically acceptable carrier.

7. A method for inducing STING-dependent type 1 interferon production in a subject, comprising: administering a composition according claim 1 to the subject in an amount sufficient to induce STING-dependent type 1 interferon production.

* * * * *